US007531168B2

(12) United States Patent
O'Hara, Jr. et al.

(10) Patent No.: US 7,531,168 B2
(45) Date of Patent: May 12, 2009

(54) METHOD FOR DOWNMODULATING IMMUNE RESPONSE IN TYPE I DIABETES

(75) Inventors: Richard M. O'Hara, Jr., Quincy, MA (US); AnnMarie Nagelin, Saugus, MA (US)

(73) Assignee: Genetics Institute LLC, Madison, NJ (US)

( * ) Notice: Subject to any disclaimer, the term of this patent is extended or adjusted under 35 U.S.C. 154(b) by 94 days.

(21) Appl. No.: 10/076,934

(22) Filed: Feb. 15, 2002

(65) Prior Publication Data
US 2003/0170232 A1    Sep. 11, 2003

Related U.S. Application Data

(60) Provisional application No. 60/269,756, filed on Feb. 16, 2001.

(51) Int. Cl.
*A61K 39/395*    (2006.01)
*C07K 16/00*    (2006.01)

(52) U.S. Cl. .............. 424/130.1; 424/133.1; 424/135.1; 424/142.1; 424/143.1; 424/154.1; 530/387.1; 530/387.3; 530/388.15; 530/388.22; 530/388.75

(58) Field of Classification Search .............. 424/134.1, 424/130.1, 133.1, 135.1, 141.1, 142.1, 143.1, 424/144.1
See application file for complete search history.

(56) References Cited

U.S. PATENT DOCUMENTS

| 5,521,288 | A | * | 5/1996 | Linsley et al. ............. 530/387.3 |
| 5,948,893 | A | | 9/1999 | June et al. ............... 530/388.75 |
| 6,685,941 | B1 | | 2/2004 | Thompson et al. |
| 2002/0006403 | A1 | * | 1/2002 | Yu et al. .................. 424/142.1 |
| 2003/0170232 | A1 | | 9/2003 | O'Hara et al. |

FOREIGN PATENT DOCUMENTS

| WO | WO 92/00092 A1 | 1/1992 |
| WO | WO 92/15671 A1 | 9/1992 |
| WO | WO 94/28912 A1 | 12/1994 |
| WO | WO 98/30232 A1 | 7/1998 |
| WO | WO 98/56401 A1 | 12/1998 |
| WO | WO 98/58965 A2 | 12/1998 |
| WO | WO 98/58965 A3 | 12/1998 |
| WO | WO-02/47721 | 6/2002 |
| WO | WO 02/051871 A2 | 7/2002 |
| WO | WO 02/051871 A3 | 7/2002 |
| WO | WO-02/066059 | 8/2002 |

OTHER PUBLICATIONS

Paul W.E., Fundamental Immunology, 1999, p. 451.*
Aly et al., Am. J. Therap., 2005, 12: 481-490.*
Blazar et al., J. Immunol., 1996, 157: 3250-3259.*
Bach J., Immunology Today, 1993, 14: 322-326.*
Beaudette-Zlatanova et al., Am J. Tranplant., 2006, 6: 857-858, Abstract.*
GenBank Acc. No. NM_006139; Homo sapiens CD28 antigen (Tp44) (CD28), mRNA.
Alvarez-Vallina, L. et al. Antigen-specific targeting of CD28-mediated T cell co-stimulation using chimeric single-chain antibody variable fragment-CD28 receptors. (Oct. 1996) *Eur. J. Immunol.* 26(10), 2304-9.
Arreaza, G.A. et al. Neonatal activation of CD28 signaling overcomes T cell anergy and prevents autoimmune diabetes by an IL-4-dependent mechanism. (Nov. 1, 1997) *J. Clin. Invest.* 100(9), 2243-53.
Aruffo, A. et al. Molecular cloning of a CD28 cDNA by a high-efficiency COS cell expression system. (Dec. 1987) *Proc. Natl. Acad. Sci. U.S.A.* 84(23), 8573-8577.
Boussiotis, V.A. et al. B7 but not intercellular adhesion molecule-1 costimulation prevents the induction of human alloantigen-specific tolerance. (Nov. 1993) *J. Exp. Med.* 178, 1753-1763.
Gilliland, L.K. et al. Rapid and reliable cloning of antibody variable regions and generation of recombinant single chain antibody fragments. (Jan. 1996) *Tissue Antigens.* 47(1), 1-20.
Gimmi, C.D. et al. B-cell surface antigen B7 provides a costimulatory signal that induces T cells to proliferate and secrete interleukin 2. (Aug. 1991) *Proc. Natl. Acad. Sci. USA.* 88, 6575-6579.
Gimmi, C.D. et al. Human T-cell clonal anergy is induced by antigen presentation in the absence of B7 costimulation. (Jul. 1993) *Proc. Natl. Acad. Sci USA* 90, 6586-6590.
Harper, K. et al. CTLA-4 and CD28 activated lymphocyte molecules are closely related in both mouse and human as to sequence, message expression, gene structure, and chromosomal location. (Aug. 1, 1991) *J. Immunol.* 147, 1037-1044.
Hayden, M.S. et al. Costimulation by CD28 sFv expressed on the tumor cell surface or as a soluble bispecific molecule targeted to the L6 carcinoma antigen. (Oct. 1996) *Tissue Antigens.* 48(4 Pt 1), 242-54.
June, C.H. et al. Role of the CD28 receptor in T-cell activation. (1990) *Immunol. Today.* 11, 211-6.
Lee, K.P. et al. The genomic organization of the CD28 gene. Implications for the regulation of CD28 mRNA expression and heterogeneity. (Jul. 1, 1990) *J. Immunol.* 145, 344-352.
Lenschow, D.J. et al. Long-term survival of xenogeneic pancreatic islet grafts induced by CTLA4Ig. (Aug. 7, 1992) *Science.* 257, 789-792.
Lenschow, D.J. et al. Differential effects of anti-B7-1 and anti-B7-2 monoclonal antibody treatment on the development of diabetes in the nonobese diabetic mouse. (Mar. 1, 1995) *J. Exp. Med.* 181(3), 1145-55.

(Continued)

*Primary Examiner*—Ilia Ouspenski
(74) *Attorney, Agent, or Firm*—DeAnn F. Smith; Foley Hoag LLP

(57) ABSTRACT

The instant invention provides compositions and methods for downmodulation of immune responses, e.g., autoimmune responses. For example, methods of downmodulating an immune response using agents that specifically block CD28-mediated signaling are provided. The subject methods are useful for both prophylactic and therapeutic downmodulation of immune responses.

21 Claims, 4 Drawing Sheets

OTHER PUBLICATIONS

Lenschow, D.J. et al. CD28/B7 regulation of Th1 and Th2 subsets in the development of autoimmune diabetes. (Sep. 1996) *Immunity*. 5(3), 285-93.

Linsley, P.S. et al. Binding of the B cell activation antigen B7 to CD28 costimulates T cell proliferation and interleukin 2 mRNA accumulation. (Mar. 1991) *J. Exp. Med.* 173, 721-730.

Turka, L.A. et al. T-cell activation by the CD28 ligand B7 is required for cardiac allograft rejection in vivo. (Nov. 1992) *Proc. Natl. Acad. Sci. USA.* 89, 11102-11105.

Winberg, G. et al. Surface expression of CD28 single chain Fv for costimulation by tumor cells. (Oct. 1996) *Immunol. Rev.* 153,209-23.

Perrin, P.J. et al. "Blockade of CD28 during in vitro activation of encephalitogenic T cells or after disease onset ameliorates experimental autoimmune encephalomyelitis," *Journal of Immunology* 163(3):1704-10 (Aug. 1999).

Silver, P.B. et al. "Blockade of costimulation through B7/CD28 inhibits experimental autoimmune uveoretinitis, but does not induce long-term tolerance," *Journal of Immunology* 165(9):5041-7 (Nov. 2000).

Tan, P. et al. "Humanization of an anti-CD28 antibody using germline human antibody sequences," *Blood* 96(11):31A (Nov. 2000).

Abe et al., "Distinct Signal Transduction in Mouse CD4+ and CD8+ Splenic T Cells After CD28 Receptor Ligation" J. Immun., 154:985-997 (1995).

Beaudette-Zlatanova et al., "Costimulation and Autoimmune Diabetes in BB rats," Am J. Transplant. 6:894-902 (2006).

Bolton et al., "Co-stimulatory Blockade—A Pathway to Tolerance?" Am. J. Trans., 6:857-858 (2006).

Dengler et al., "Prolonged Allograft Survival But No Tolerance Induction by Modulating CD28 Antibody JJ319 After High-Responder Rat Heart Transplantation" Transplantation, 67(3):392-398 (1999).

Jang, M.S. et al., "A Blocking Anti-CD28-Specific Antibody Induces Long-Term Heart Allograft Survival by Suppression of the PKC-JNK Signal Pathway," Transplantation, 85(7):1051-1055 (2008).

Laskowski, I.A. et al., "Anti-CD28 Monoclonal Antibody Therapy Prevents Chronic Rejection of Renal Allografts in Rats," J. Am. Soc. Nephrol, 13:519-527 (2002).

Luo, Z.J. et al., "Anergic T Cells Generated in Vitro Suppress Rejection Response to Iselt Allografts", 69(10):2144-2148 (2000).

Nagelin, J.D. et al., "An Anti-CD28 Single Chain Antibody Prevents Diabetes Onset in NOD Mice," FASEB Journal, Fed. of American Soc. for Experimental Biology, 15(5):A211 (2001) Abstract Only.

International Search Report for PCT/US2008/071752 dated Oct. 17, 2008.

* cited by examiner

SEQUENCE LISTING

```
<160> NUMBER OF SEQ ID NOS: 2

<210> SEQ ID NO 1
<211> LENGTH: 3803
<212> TYPE: DNA
<213> ORGANISM: Homo sapiens

<400> SEQUENCE: 1
taaagtcatc aaaacaacgt tatatcctgt gtgaaatgct gcagtcagga tgccttgtgg      60
ttgagtgcct tgatcatgtg ccctaagggg atggtggcgg tggtggtggc cgtggatgac     120
```

```
ggagactctc aggccttggc aggtgcgtct ttcagttccc ctcacacttc gggttcctcg    180
gggaggaggg gctggaaccc tagcccatcg tcaggacaaa gatgctcagg ctgctcttgg    240
ctctcaactt attcccttca attcaagtaa caggaaacaa gattttggtg aagcagtcgc    300
ccatgcttgt agcgtacgac aatgcggtca accttagctg caagtattcc tacaatctct    360
tctcaaggga gttccgggca tcccttcaca aaggactgga tagtgctgtg gaagtctgtg    420
ttgtatatgg gaattactcc cagcagcttc aggtttactc aaaaacgggg ttcaactgtg    480
atgggaaatt gggcaatgaa tcagtgacat tctacctcca gaatttgtat gttaaccaaa    540
cagatattta cttctgcaaa attgaagtta tgtatcctcc tccttaccta gacaatgaga    600
agagcaatgg aaccattatc catgtgaaag ggaaacacct ttgtccaagt cccctatttc    660
ccggaccttc taagcccttt tgggtgctgg tggtggttgg tggagtcctg gcttgctata    720
gcttgctagt aacagtggcc tttattattt tctgggtgag gagtaagagg agcaggctcc    780
tgcacagtga ctacatgaac atgactcccc gccgccccgg gcccacccgc aagcattacc    840
agccctatgc cccaccacgc gacttcgcag cctatcgctc ctgacacgga cgcctatcca    900
gaagccagcc ggctggcagc ccccatctgc tcaatatcac tgctctggat aggaaatgac    960
cgccatctcc agccggccac ctcaggcccc tgttgggcca ccaatgccaa ttttttctcga   1020 gtgactagac caaatatcaa gatcattttg agactctgaa atgaagtaaa agagatttcc   1080
tgtgacaggc caagtcttac agtgccatgg cccacattcc aacttaccat gtacttagtg   1140
acttgactga gaagttaggg tagaaaacaa aaagggagtg gattctggga gcctcttccc   1200
tttctcactc acctgcacat ctcagtcaag caaagtgtgg tatccacaga catttttagtt   1260 gcagaagaaa ggctaggaaa tcattccttt tggttaaatg ggtgtttaat cttttggtta   1320
gtgggttaaa cggggtaagt tagagtaggg ggagggatag gaagacatat ttaaaaacca   1380
ttaaaacact gtctcccact catgaaatga gccacgtagt tcctatttaa tgctgttttc   1440
ctttagttta gaaatacata gacattgtct tttatgaatt ctgatcatat ttagtcattt   1500
tgaccaaatg agggatttgg tcaaatgagg gattccctca aagcaatatc aggtaaacca   1560
agttgctttc ctcactccct gtcatgagac ttcagtgtta atgttcacaa tatactttcg   1620
aaagaataaa atagttctcc tacatgaaga aagaatatgt caggaaataa ggtcacttta   1680
tgtcaaaatt atttgagtac tatgggacct ggcgcagtgg ctcatgcttg taatcccagc   1740
actttgggag gccgaggtgg gcagatcact tgagatcagg accagcctgg tcaagatggt   1800
gaaactccgt ctgtactaaa aatacaaaat ttagcttggc ctggtggcag gcacctgtaa   1860
tcccagctgc ccaggaggct gaggcatgag aatcgcttga acctggcagg cggaggttgc   1920
agtgagccga gatagtgcca cagctctcca gcctgggcga cagagtgaga ctccatctca   1980
aacaacaaca acaacaacaa caacaacaac aaaccacaaa attatttgag tactgtgaag   2040
gattatttgt ctaacagttc attccaatca gaccaggtag gagctttcct gtttcatatg   2100
tttcagggtt gcacagttgg tctctttaat gtcggtgtgg agatccaaag tgggttgtgg   2160
aaagagcgtc cataggagaa gtgagaatac tgtgaaaagg gatgttagca ttcattagag   2220
tatgaggatg agtcccaaga aggttctttg gaaggaggac gaatagaatg gagtaatgaa   2280
attcttgcca tgtgctgagg agatagccag cattaggtga caatcttcca gaagtggtca   2340
ggcagaaggt gccctggtga gagctccttt acagggactt tatgtggttt agggctcaga   2400
gctccaaaac tctgggctca gctgctcctg taccttggag gtccattcac atgggaaagt   2460
attttggaat gtgtcttttg aagagagcat cagagttctt aagggactgg gtaaggcctg   2520
```

```
accctgaaat gaccatggat attttctac ctacagtttg agtcaactag aatatgcctg    2580
gggaccttga agaatgccct tcagtggccc tcaccatttg ttcatgcttc agttaattca    2640
ggtgttgaag gagcttaggt tttagaggca cgtagacttg gttcaagtct cgttagtagt    2700
tgaatagcct caggcaagtc actgcccacc taagatgatg gttcttcaac tataaatgga    2760
gataatggtt acaaatgtct cttcctatag tataatctcc ataagggcat ggcccaagtc    2820
tgtctttgac tctgcctatc cctgacgttt agtagcatgc ccgacataca atgttagcta    2880
ttggtattat tgccatatag ataaattatg tataaaaatt aaactgggca atagcctaag    2940 aagggggaa tattgtaaca caaatttaaa cccactacgc agggatgagg tgctataata    3000
tgaggacctt ttaacttcca tcattttcct gtttcttgaa atagtttatc ttgtaatgaa    3060
atataaggca cctcccactt ttatgtatag aaagaggtct tttaatttt ttttaatgtg    3120 agaaggaagg gaggagtagg aatcttgaga ttccatatcg aaaatactgt actttggttg    3180 attttaagt gggcttccat tccatggatt taatcagtcc caagaagatc aaactcagca    3240
gtacttgggt gctgaagaac tgttggattt accctggcac gtgtgccact tgcccagctt    3300
cttgggcaca cagagttctt caatccaagt tatcagattg tatttgaaaa tgacagagct    3360
ggagagtttt ttgaaatggc agtggcaaat aaataaatac tttttttaa atggaaagac    3420 ttgatctatg gtaataaatg attttgtttt ctgactggaa aaataggcct actaaagatg    3480
aatcacactt gagatgtttc ttactcactc tgcacagaaa caaagaagaa atgttataca    3540
gggaagtccg ttttcactat tagtatgaac caagaaatgg ttcaaaaaca gtggtaggag    3600
caatgctttc atagtttcag atatggtagt tatgaagaaa acaatgtcat tgctgctat     3660 tattgtaaga gtcttataat taatggtact cctataattt ttgattgtga gctcacctat    3720
ttgggttaag catgccaatt taaagagacc aagtgtatgt acattatgtt ctacatattc    3780
agtgataaaa ttactaaact act                                            3803
```

<210> SEQ ID NO 2
<211> LENGTH: 219
<212> TYPE: PRT
<213> ORGANISM: Homo sapiens

<400> SEQUENCE: 2

```
Met Leu Arg Leu Leu Leu Ala Leu Asn Leu Phe Pro Ser Ile Gln Val
 1               5                  10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140
```

```
                                          -continued

Leu Phe Pro Gly Pro Ser Lys Pro Phe Trp Val Leu Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Tyr Arg Ser
    210                 215
```

METHOD FOR DOWNMODULATING IMMUNE RESPONSE IN TYPE I DIABETES

RELATED APPLICATIONS

This application claims priority to U.S. Ser. No. 60/269,756, filed on Feb. 16, 2001. The entire contents of that application are incorporated herein by reference.

BACKGROUND OF THE INVENTION

In order for T cells to respond to foreign proteins, two signals must be provided by antigen-presenting cells (APCs) to resting T lymphocytes (Jenkins, M. and Schwartz, R. (1987) *J. Exp. Med.* 165, 302-319; Mueller, D. L., et al. (1990) *J. Immunol.* 144, 3701-3709). The first signal, which confers specificity to the immune response, is transduced via the T cell receptor (TCR) following recognition of foreign antigenic peptide presented in the context of the major histocompatibility complex (MHC). Polyclonal activators (e.g., anti-CD3 antibodies can also be used to transmit primary activation signals. The second signal, termed costimulation, induces T cells to proliferate and become functional (Lenschow et al. 1996. *Annu. Rev. Immunol.* 14:233). Costimulation is neither antigen-specific, nor MHC restricted and is thought to be provided by one or more distinct cell surface molecules expressed by APCs (Jenkins, M. K., et al. 1988 *J. Immunol.* 140, 3324-3330; Linsley, P. S., et al. 1991 *J. Exp. Med.* 173, 721-730; Gimmi, C. D., et al., 1991 *Proc. Natl. Acad. Sci. USA.* 88, 6575-6579; Young, J. W., et al. 1992 *J. Clin. Invest.* 90, 229-237; Koulova, L., et al. 1991 *J. Exp. Med.* 173, 759-762; Reiser, H., et al. 1992 *Proc. Natl. Acad. Sci. USA.* 89, 271-275; van-Seventer, G. A., et al. (1990) *J. Immunol.* 144, 4579-4586; LaSalle, J. M., et al., 1991 *J. Immunol.* 147, 774-80; Dustin, M. I., et al., 1989 *J. Exp. Med.* 169, 503; Armitage, R. J., et al. 1992 *Nature* 357, 80-82; Liu, Y., et al. 1992 *J. Exp. Med.* 175, 437-445).

The CD80 (B7-1) and CD86 (B7-2) proteins, expressed on APCs, are critical costimulatory molecules (Freeman et al. 1991. *J. Exp. Med.* 174:625; Freeman et al. 1989 *J. Immunol.* 143:2714; Azuma et al. 1993 *Nature* 366:76; Freeman et al. 1993. *Science* 262:909). B7-2 appears to play a predominant role during primary immune responses, while B7-1, which is upregulated later in the course of an immune response, may be important in prolonging primary T cell responses or costimulating secondary T cell responses (Bluestone. 1995. *Immunity.* 2:555).

One ligand to which B7-1 and B7-2 bind, CD28, is constitutively expressed on resting T cells and increases in expression after activation. After signaling through the T cell receptor, ligation of CD28 and transduction of a costimulatory signal induces T cells to proliferate and secrete IL-2 (Linsley, P. S., et al. 1991 *J. Exp. Med.* 173, 721-730; Gimmi, C. D., et al. 1991 *Proc. Natl. Acad. Sci. USA.* 88, 6575-6579; June, C. H., et al. 1990 *Immunol. Today.* 11, 211-6; Harding, F. A., et al. 1992 *Nature.* 356, 607-609). A second ligand, termed CTLA4 (CD152) is homologous to CD28 but is not expressed on resting T cells and appears following T cell activation (Brunet, J. F., et al., 1987 *Nature* 328, 267-270). CTLA4 appears to be critical in negative regulation of T cell responses (Waterhouse et al. 1995. *Science* 270:985). Blockade of CTLA4 has been found to remove inhibitory signals, while aggregation of CTLA4 has been found to provide inhibitory signals that downregulate T cell responses (Allison and Krummel. 1995. *Science* 270:932). The B7 molecules have a higher affinity for CTLA4 than for CD28 (Linsley, P. S., et al., 1991 *J. Exp. Med.* 174, 561-569) and B7-1 and B7-2 have been found to bind to distinct regions of the CTLA4 molecule and have different kinetics of binding to CTLA4 (Linsley et al. 1994. *Immunity.* 1:793). A new molecule related to CD28 and CTLA4, ICOS, has been identified (Hutloff et al. 1999. *Nature.* 397:263; WO 98/38216).

The importance of the B7:CD28/CTLA4 costimulatory pathway has been demonstrated in vitro and in several in vivo model systems. Blockade of this costimulatory pathway results in the development of antigen specific tolerance in murine and human systems (Harding, F. A., et al. (1992) *Nature.* 356, 607-609; Lenschow, D. J., et al. (1992) *Science.* 257, 789-792; Turka, L. A., et al. (1992) *Proc. Natl. Acad. Sci. USA.* 89, 11102-11105; Gimmi, C. D., et al. (1993) *Proc. Natl. Acad. Sci USA* 90, 6586-6590; Boussiotis, V., et al. (1993) *J. Exp. Med.* 178, 1753-1763). Conversely, expression of B7 by B7 negative murine tumor cells induces T-cell mediated specific immunity accompanied by tumor rejection and long lasting protection to tumor challenge (Chen, L., et al. (1992) *Cell* 71, 1093-1102; Townsend, S. E. and Allison, J. P. (1993) *Science* 259, 368-370; Baskar, S., et al. (1993) *Proc. Natl. Acad. Sci.* 90, 5687-5690.).

Despite the structural similarities and shared affinity for the ligands B7-1 (CD80) and B7-2 (CD86) it is now clear that CD28 and CTLA-4 (CD152) and mediate essentially opposing effects on T cell activation. While the CD28/B7 interaction is known to serve as a positive co-stimulator in the context of TCR engagement by MHC/antigen complex, CTLA-4/B7 is now recognized as imposing a negative effect on cell cycle progression, IL-2 production, and proliferation of T cells following activation.

The development of novel methods for modulating the activities of CD28 and/or CTLA4 would be of great benefit in modulating the immune response. In addition, owing to the opposing effects of engagement of CD28 and CTLA4, specific compositions and methods for separately manipulating one or the other molecule on T cells would be beneficial. In particular, methods of specifically downmodulating T cell responses by modulating the CD28 pathway, while leaving the downmodulatory CTLA4 pathway intact would be beneficial in suppressing immune responses.

SUMMARY OF THE INVENTION

CD28 has been shown to be important in transmitting a costimulatory signal to T cells and, thereby, regulating T cell activation. The use of anti-CD28 antibodies in the stimulation of immune responses was known in the art (e.g., U.S. Pat. No. 5,948,893). The instant invention is based, at least in part, on the discovery that agents that specifically block CD28-mediated signaling, for example, antigen-binding portions of antibodies, such as scFv molecules, are useful in downmodulating the immune response, both in vitro and in vivo. The instant examples demonstrate that antigen-binding portions of CD28 antibodies are effective in preventing the onset of diabetes in NOD mice, a well accepted animal model for the autoimmune disease human type I (immune mediated) diabetes. Both two to three week old animals and adult animals were found to be protected by treatment with anti-CD28 scFv.

Accordingly, in one aspect, the invention relates to a method of therapeutically downmodulating an autoimmune response in a subject by administering an antigen binding portion of an anti-CD28 antibody that blocks signaling via CD28 to the subject such that an autoimmune response in the subject is downmodulated.

In one embodiment, the antigen binding portion is an scFv molecule or an Fab fragment.

In one embodiment, the antigen binding portion is humanized. In another embodiment, the antigen binding portion is fully human.

In another aspect, the invention pertains to a method of therapeutically downmodulating an autoimmune response in a subject comprising administering a small molecule that specifically blocks signaling via CD28 to the subject such that an autoimmune response in the subject is downmodulated.

In one embodiment, the autoimmune response is mediated by CD4+ T cells. In another embodiment, the autoimmune response is mediated by CD8+ T cells.

In one embodiment, the autoimmune response is type I diabetes.

In another aspect, the invention pertains to a method of therapeutically downmodulating an ongoing autoimmune response in a subject by administering an antigen binding portion of an anti-CD28 antibody that blocks signaling via CD28 to the subject such that an ongoing autoimmune response in the subject is downmodulated.

In one embodiment, the antigen binding portion is a scFv molecule or an Fab fragment.

In one embodiment, the antigen-binding portion is humanized. In another embodiment, the antigen-binding portion is fully human.

In still another aspect, the invention pertains to a method of therapeutically downmodulating an ongoing autoimmune response in a subject by administering a small molecule that specifically blocks signaling via CD28 to the subject such that an ongoing autoimmune response in the subject is downmodulated.

In one embodiment, the autoimmune response is mediated by CD4+ T cells. In another embodiment, the autoimmune response is mediated by CD8+ T cells.

In one embodiment, the autoimmune response is type I diabetes.

In another aspect, the invention pertains to a method of prophylactically downmodulating an autoimmune response in a subject by administering an antigen binding portion of an anti-CD28 antibody that blocks signaling via CD28 to the subject such that an autoimmune response in the subject is downmodulated or delayed in its onset.

In one embodiment, the antigen binding portion is a scFv molecule or an Fab fragment.

In one embodiment, the antigen-binding portion is humanized. In another embodiment, the antigen-binding portion is fully human.

In yet another aspect, the invention pertains to a method of prophylactically downmodulating an autoimmune response in a subject comprising administering a small molecule that specifically blocks signaling via CD28 to the subject such that an autoimmune response in the subject is downmodulated or delayed in its onset.

In one embodiment, the autoimmune response is mediated by CD4+ T cells. In another embodiment, the autoimmune response is mediated by CD8+ T cells.

In one embodiment, the autoimmune response is type I diabetes.

DETAILED DESCRIPTION OF THE INVENTION

Figure 1:
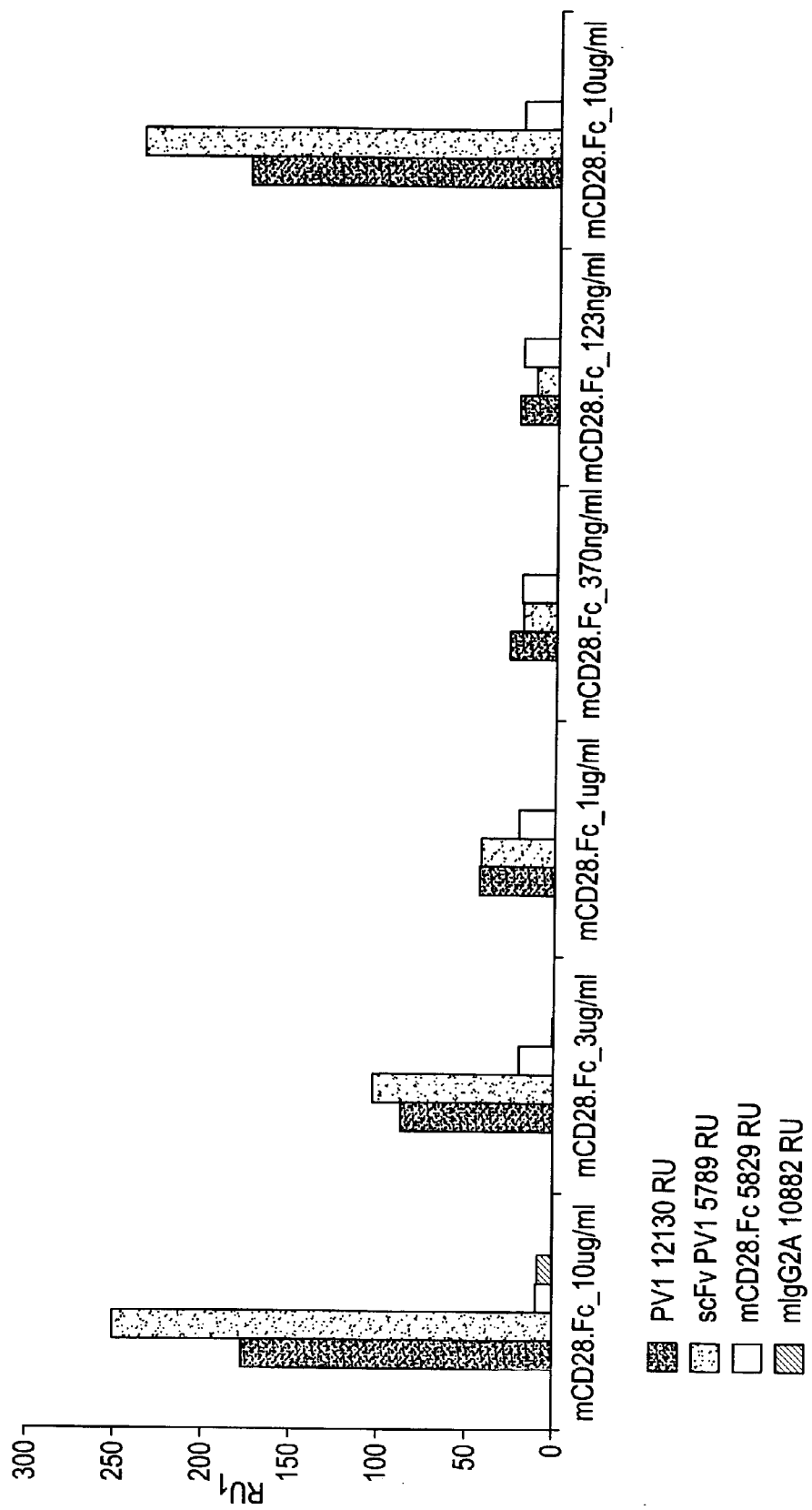
FIG. 1 shows that anti-CD28 and PV1 (anti-CD28) scFv bind to CD28 equally.

As set forth briefly above, the instant invention pertains, at least in part, to methods of downmodulating the immune response using molecules that specifically block CD28-mediated signaling, e.g., scFv of anti-CD28 antibodies.

Various aspects of the invention are described in further detail in the following subsections:

I. Definitions

The term "subject" as used herein refers to vertebrate hosts, particularly to mammals, and includes, but is not limited to, primates, including humans, and domestic animals.

As used herein, the term "immune response" includes T cell mediated and/or B cell mediated immune responses that are influenced by modulation of T cell costimulation. Exemplary immune responses include T cell responses, e.g., proliferation, cytokine production, and cellular cytotoxicity. In addition, the term immune response includes immune responses that are indirectly effected by T cell activation, e.g., antibody production (humoral responses) and activation of cytokine responsive cells, e.g., macrophages.

As used herein, the term "primary immune response" includes immune responses to antigens which have not been seen before by a subject, e.g., to which the subject is naïve.

As used herein, the term "secondary immune response" includes immune responses to antigens which have been seen before by a subject, e.g., to which the subject has been primed. The tem "ongoing immune response" includes an immune response to a certain antigen which is ongoing, e.g, is presently active and detectable.

As used herein, the term "prophylactically" includes the administration of an effective molecule of the inveniton before the onset of an undesirable immune response.

As used herein, the term "therapeutically" includes the includes the administration of an effective molecule of the inveniton to treat an existing or ongoing unwanted immune response (e.g., an autoimmune response) which would benefit by treatment with the agent.

As used here, the term "self" with reference to a peptide includes peptides which are not foreign to a subject and to which an autoimmune response can occur. The immune system can normally discriminate between self and non-self ("foreign"). Optimally, the mammalian immune system is non-reactive (e.g., tolerant) to self-antigens. The mechanisms that provide tolerance normally eliminate or render inactive clones of B and T cells that would otherwise carry out anti-self reactions. Autoimmune diseases or disorders (e.g., multiple sclerosis, rheumatoid arthritis, lupus erythematosus, and Type I diabetes mellitus) represent an aberrant immune attack in which antibodies or T cells of a host are directed against self-antigen not normally the target of the immune response. Autoimmunity results from the dysfunction of normal mechanisms of self-tolerance that prevent the production of functional self-reactive clones of B and T cells.

As used herein, the term "costimulate" with reference to activated T cells includes the ability of a costimulatory molecule to provide a second, non-activating receptor mediated signal (a "costimulatory signal") that induces proliferation or effector function. For example, a costimulatory signal can result in cytokine secretion, e.g., in a T cell that has received a T cell-receptor-mediated signal. T cells that have received a cell-receptor mediated signal, e.g., via a T cell receptor (TCR)

(e.g., by an antigen or by a polyclonal activator) are referred to herein as "activated T cells."

For example, T cell receptors are present on T cells and are associated with CD3 molecules. T cell receptors are stimulated by antigen in the context of MHC molecules (as well as by polyclonal T cell activating reagents). T cell activation via the TCR results in numerous changes, e.g., protein phosphorylation, membrane lipid changes, ion fluxes, cyclic nucleotide alterations, RNA transcription changes, protein synthesis changes, and cell volume changes, and expression of activation markers, e.g., CTLA4.

Transmission of a costimulatory signal to a T cell (e.g., via cross-linked CD28 molecules) involves a signaling pathway that is not inhibited by cyclosporin A. In addition, a costimulatory signal can induce cytokine secretion (e.g., IL-2 and/or IL-10) in a T cell and/or can prevent the induction of unresponsiveness to antigen, the induction of anergy, or the induction of cell death in the T cell.

A "CD28-mediated signal" includes one or more cellular events directly or indirectly induced in an immune cell which expresses CD28 on its surface by the binding of a ligand that activates (e.g., crosslinks) the cell surface CD28. Activation of CD28 receptor(s) triggers a signaling event(s) which results in a measurable cellular change. CD28-mediated signaling can be detected, for instance, by measuring commonly measured parameters of T cell costimulation in an in vitro assay. Under the appropriate circumstances CD28-mediated signaling results in the upmodulation of an immune response by the immune cell. Blockade of CD28-mediated signaling results in the downmodulation of an immune response by the immune cell. An agent which binds to CD28 to effectively block a CD28-mediated signal (e.g., by blocking ligand binding) without itself activating the CD28 receptor (e.g., via aggregation of the receptor) will effectively block CD28-mediated signaling. Preferably, an agent specifically blocks CD28-mediated signaling, i.e., blocks a signal transmitted by CD28, while not blocking a signal transmitted by another cell surface molecule, e.g., CTLA4.

As used herein, the term "inhibitory signal" refers to a signal transmitted via an inhibitory receptor (e.g., CTLA4) on an immune cell. Such a signal antagonizes a signal transmitted via an activating receptor (e.g., via a TCR) and can result in, e.g., inhibition of second messenger generation; inhibition of proliferation; inhibition of effector function in the immune cell, (e.g., reduced cellular cytotoxicity) the failure of the immune cell to produce mediators, (such as cytokines (e.g., IL-2) and/or mediators of allergic responses); or the development of anergy.

As used herein, the term "unresponsiveness" includes refractivity of immune cells to stimulation, e.g., stimulation via an activating receptor or a cytokine. Unresponsiveness can occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory molecule) results in failure to produce cytokines and, thus, failure to proliferate. Anergic T cells can, however, mount responses to unrelated antigens and can proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. 1992. Science. 257:1134).

As used herein, the term "activity" with respect to a polypeptide includes activities which are inherent in the structure of a polypeptide. With respect to CD28, the term "activity" includes the ability of a CD28 polypeptide to bind to a costimulatory molecule (e.g., CD80 or CD86) and/or to modulate a costimulatory signal in an activated immune cell, e.g., by engaging a natural ligand on an antigen presenting cell. CD28 transmits a costimulatory signal to a T cell. Modulation of an costimulatory signal in a T cell results in modulation of proliferation of and/or cytokine secretion by the T cell. CD28 can also modulate a costimulatory signal by competing with an inhibitory receptor for binding of costimulatory molecules, e.g., CTLA4. Thus, the term "CD28 activity" includes the ability of a CD28 polypeptide to bind its natural ligand(s), the ability to modulate immune cell costimulatory or inhibitory signals, and the ability to modulate the immune response.

The term "antibody", as used herein, is intended to refer to immunoglobulin molecules comprised of four polypeptide chains, two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The phrase "complementary determining region" (CDR) includes the region of an antibody molecule which comprises the antigen binding site.

The antibody may be an IgG such as IgG1, IgG2, IgG3 or IgG4; or IgM, IgA, IgE or IgD isotype. The constant domain of the antibody heavy chain may be selected depending upon the effector function desired. The light chain constant domain may be a kappa or lambda constant domain.

The term "antigen-binding portion", as used herein, refers to one or more fragments of an antibody that retain the ability to specifically bind to an antigen (e.g., human CD28). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv ("scFv"); see e.g., Bird et al. (1988) *Science* 242:423-426; and Huston et al. (1988) *Proc. Natl. Acad. Sci. USA* 85:5879-5883). Such single chain antibodies (scFvs) are preferred molecules intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123). Preferably, the antigen-binding fragments do not cross-link the antigen to which they bind.

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

Antibodies may be polyclonal or monoclonal; xenogeneic, allogeneic, or syngeneic; or modified forms thereof, e.g. humanized, chimeric, etc. Preferably, antibodies of the invention bind specifically or substantially specifically to CD28 molecules present on a T cell of a subject. The terms "monoclonal antibodies" and "monoclonal antibody composition", as used herein, refer to a population of antibody molecules that contain only one species of an antigen binding site capable of immunoreacting with a particular epitope of an antigen, whereas the term "polyclonal antibodies" and "polyclonal antibody composition" refer to a population of antibody molecules that contain multiple species of antigen binding sites capable of interacting with a particular antigen. A monoclonal antibody composition, typically displays a single binding affinity for a particular antigen with which it immunoreacts.

The term "humanized antibody", as used herein, is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

An "isolated antibody", as used herein, is intended to refer to an antibody that is substantially free of other antibodies having different antigenic specificities (e.g., an isolated antibody that specifically binds CD28 is substantially free of antibodies that specifically bind antigens other than CD28). Moreover, an isolated antibody may be substantially free of other cellular material and/or chemicals.

"Anti-CD28 antibodies" are antibodies that specifically bind to a site on the extracellular domain of CD28 protein, and modulate a costimulatory signal to a T cell. The term "anti-CD28 antibodies" includes antibodies that block the binding of CD28 to costimulatory molecules, e.g. CD80 and/or CD86.

The phrase "specifically" with reference to binding, recognition, or reactivity of antibodies includes antibodies which bind to naturally occurring molecules which are expressed transiently only on activated T cells. In particular, with respect to CD28, the term "specifically" with reference to binding, recognition, or reactivity of antibodies includes anti-CD28 antibodies that bind to naturally occurring forms of CD28, but are substantially unreactive with molecules related to CD28, such as CTLA4 and other members of the immunoglobulin superfamily. The phrase "substantially unreactive" includes antibodies which display no greater binding to molecules related to CD28, e.g., CTLA4 (but excluding CD28 molecules) as compared to unrelated molecules, e.g., CD27. Preferably, such antibodies bind to molecules related to CD28 (but excluding CD28 molecules) with only background binding. Antibodies specific for CD28 from one source, e.g., human CD28 may or may not be reactive with CD28 molecules from different species. Antibodies specific for naturally occurring CD28 may or may not bind to mutant forms of such molecules. In one embodiment, mutations in the amino acid sequence of a naturally occurring CD28 molecule result in modulation of the binding (e.g., either increased or decreased binding) of the antibody to the CD28 molecule. Antibodies to CD28 can be readily screened for their ability to meet this criteria. Assays to determine affinity and specificity of binding are known in the art, including competitive and non-competitive assays. Assays of interest include ELISA, RIA, flow cytometry, etc. Binding assays may use purified or semi-purified CD28 protein, or alternatively may use cells that express CD28, e.g. cells transfected with an expression construct for CD28; T cells that have been stimulated through cross-linking of CD3 or the addition of irradiated allogeneic cells, etc. As an example of a binding assay, purified CD28 protein is bound to an insoluble support, e.g. microtiter plate, magnetic beads, etc. The candidate antibody and soluble, labeled CD80 or CD86 are added to the cells, and the unbound components are then washed off. The ability of the antibody to compete with CD80 and CD86 for CD28 binding is determined by quantitation of bound, labeled CD80 or CD86. Confirmation that the blocking agent does not cross-react with CTLA4 may be performed with a similar assay, substituting CTLA4 for CD28. An isolated antibody that specifically binds human CD28 may, however, have cross-reactivity to other antigens, such as CD28 molecules from other species.

Antigen binding portions of anti-CD28 antibodies can be administered to patients or cells of a patient can be caused to express such molecules, e.g., in soluble form. As used herein, the term "causing to express" with reference to an antibody or antibody biding portion includes art recognized methods by which a cell can be made to express a particular molecule. For example, methods such as transfection can be used to cause a cell to express an antigen binding portion of an anti-CD28 molecule (e.g., an antigen binding portion of an anti-CD28 antibody or an MHC molecule).

For example, DNA can be introduced into cells of a subject via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual*. 2nd, ed., Cold Spring Harbor Laboratory, Cold Spring Harbor Laboratory Press, Cold Spring Harbor, NY, 1989), and other laboratory manuals.

As used herein, a "naturally-occurring" nucleic acid molecule refers to an RNA or DNA molecule having a nucleotide sequence that occurs in nature (e.g., encodes a natural protein).

As used herein, the term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

As used herein, the term "vector" refers to a nucleic acid molecule capable of transporting another nucleic acid molecule to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

As used herein, the term "host cell" is intended to refer to a cell into which a nucleic acid molecule of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, an "isolated protein" refers to a protein that is substantially free of other proteins, cellular material and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the protein is derived, or substantially free from chemical precursors or other chemicals when chemically synthesized. The language "substantially free of cellular material" includes preparations of protein in which the protein is separated from cellular components of the cells from which it is isolated or recombinantly produced. In one embodiment, the language "substantially free of cellular material" includes preparations of protein having less than about 30% (by dry weight) of contaminating protein (e.g., non-CD28 or non-anti-CD28 antibody), more preferably less than about 20% of contaminating protein, still more preferably less than about 10% of contaminating protein, and most preferably less than about 5% contaminating protein. When the CD28 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of protein in which the protein is separated from chemical precursors or other chemicals which are involved in the synthesis of the protein. In one embodiment, the language "substantially free of chemical precursors or other chemicals" includes preparations of protein having less than about 30% (by dry weight) of chemical precursors or contaminating chemicals, more preferably less than about 20% chemical precursors or contaminating chemicals, still more preferably less than about 10% chemical precursors or contaminating chemicals, and most preferably less than about 5% chemical precursors or contaminating chemicals.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid molecule and the amino acid sequence encoded by that nucleic acid molecule, as defined by the genetic code.

```
                        GENETIC CODE

Alanine         (Ala,  A) GCA, GCC, GCG, GCT
Arginine        (Arg,  R) AGA, ACG, CGA, CGC, CGG, CGT
Asparagine      (Asn,  N) AAC, AAT
Aspartic acid   (Asp,  D) GAC, GAT
Cysteine        (Cys,  C) TGC, TGT
Glutamic acid   (Glu,  E) GAA, GAG
Glutamine       (Gln,  Q) CAA, CAG
Glycine         (Gly,  G) GGA, GGC, GGG, GGT
Histidine       (His,  H) CAC, CAT
Isoleucine      (Ile,  I) ATA, ATC, ATT
Leucine         (Leu,  L) CTA, CTC, CTG, CTT, TTA, TTG
Lysine          (Lys,  K) AAA, AAG
Methionine      (Met,  M) ATG
Phenylalanine   (Phe,  F) TTC, TTT
Proline         (Pro,  P) CCA, CCC, CCG, CCT
Serine          (Ser,  S) AGC, AGT, TCA, TCC, TCG, TCT
Threonine       (Thr,  T) ACA, ACC, ACG, ACT
Tryptophan      (Trp,  W) TGG
Tyrosine        (Tyr,  Y) TAC, TAT
Valine          (Val,  V) GTA, GTC, GTG, GTT
Termination     (end)     TAA, TAG, TGA
signal
```

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA molecule coding for a CD28 polypeptide or CD28 antibody of the invention (or any portion thereof) can be used to derive the CD28 polypeptide amino acid sequence or CD28 antibody amino acid sequence, using the genetic code to translate the CD28 polypeptide or CD28 antibody molecule into an amino acid sequence. Likewise, for any CD28 polypeptide or CD28 antibody—amino acid sequence, corresponding nucleotide sequences that can encode CD28 polypeptide or CD28 antibody protein can be deduced from the genetic code (which, because of its redundancy, will produce multiple nucleic acid sequences for any given amino acid sequence).

Thus, description and/or disclosure herein of a nucleotide sequence encoding a CD28 polypeptide or a nucleotide sequence encoding a CD28 antibody should be considered to also include description and/or disclosure of the amino acid sequence encoded by the nucleotide sequence. Similarly, description and/or disclosure of a CD28 polypeptide or CD28 antibody amino acid sequence herein should be considered to also include description and/or disclosure of all possible nucleotide sequences that can encode the amino acid sequence.

II. Agents that Specifically block CD28-mediated Signaling

A. Anti-CD28 Antibodies

Antibodies typically comprise two heavy chains linked together by disulfide bonds and two light chains. Each light chain is linked to a respective heavy chain by disulfide bonds. Each heavy chain has at one end a variable domain followed by a number of constant domains. Each light chain has a variable domain at one end and a constant domain at its other end. The light chain variable domain is aligned with the variable domain of the heavy chain. The light chain constant domain is aligned with the first constant domain of the heavy chain. The constant domains in the light and heavy chains are not involved directly in binding the antibody to antigen. The variable domains of each pair of light and heavy chains form the antigen binding site.

The domains on the light and heavy chains have the same general structure and each domain comprises a framework of four regions, whose sequences are relatively conserved, connected by three complementarity determining regions (CDRs). The four framework regions largely adopt a beta-sheet conformation and the CDRs form loops connecting, and in some cases forming part of, the beta-sheet structure. The CDRs are held in close proximity by the framework regions and, with the CDRs from the other domain, contribute to the formation of the antigen binding site. CDRs and framework regions of antibodies may be determined by reference to Kabat et al ("Sequences of proteins of immunological interest" U.S. Dept. of Health and Human Services, U.S. Government Printing Office, 1987).

Polyclonal anti-CD28 antibodies can be prepared as described above by immunizing a suitable subject with a CD28 immunogen. The anti-CD28 antibody titer in the immunized subject can be monitored over time by standard techniques, such as with an enzyme linked immunosorbent assay (ELISA) using immobilized a CD28 polypeptide. If desired, the antibody molecules directed against a CD28 polypeptide can be isolated from the mammal (e.g., from the blood) and further purified by well known techniques, such as protein A chromatography to obtain the IgG fraction. At an appropriate time after immunization, e.g., when the anti-CD28 antibody titers are highest, antibody-producing cells can be obtained from the subject and used to prepare monoclonal antibodies by standard techniques, such as the hybridoma technique originally described by Kohler and Milstein (1975, Nature 256:495-497) (see also, Brown et al. (1981) J. Immunol 127:539-46; Brown et al. (1980) J Biol Chem 255: 4980-83; Yeh et al. (1976) PNAS 76:2927-31; and Yeh et al. (1982) Int. J. Cancer 29:269-75), the more recent human B cell hybridoma technique (Kozbor et al. (1983) Immunol Today 4:72), the EBV-hybridoma technique (Cole et al. (1985), Monoclonal Antibodies and Cancer Therapy, Alan R. Liss, Inc., pp. 77-96) or trioma techniques. The technology for producing monoclonal antibody hybridomas is well known (see generally R. H. Kenneth, in Monoclonal Antibodies: A New Dimension In Biological Analyses, Plenum Publishing Corp., New York, N.Y. (1980); E. A. Lerner (1981) Yale J. Biol. Med., 54:387-402; M. L. Gefter et al. (1977) Somatic Cell Genet., 3:231-36). Briefly, an immortal cell line (typically a myeloma) is fused to lymphocytes (typically splenocytes) from a mammal immunized with a CD28 immunogen as described above, and the culture supernatants of the resulting hybridoma cells are screened to identify a hybridoma producing a monoclonal antibody that binds specifically to a CD28 polypeptide.

Any of the many well known protocols used for fusing lymphocytes and immortalized cell lines can be applied for the purpose of generating an anti-CD28 monoclonal antibody (see, e.g., G. Galfre et al. (1977) Nature 266:55052; Gefter et al. Somatic Cell Genet., cited supra; Lerner, Yale J. Biol. Med., cited supra; Kenneth, Monoclonal Antibodies, cited supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a CD28 molecule, e.g., using a standard ELISA assay.

As an alternative to preparing monoclonal antibody-secreting hybridomas, a monoclonal anti-CD28 antibody can be identified and isolated by screening a recombinant combinatorial immunoglobulin library (e.g., an antibody phage display library) with CD28 (or a portion of a CD28 molecule, e.g., the extracellular domain of CD28) to thereby isolate immunoglobulin library members that bind a CD28 polypeptide. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J* 12:725-734; Hawkins et al. (1992) *J Mol Biol* 226:889-896; Clarkson et al. (1991) *Nature* 352: 624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; Barbas et al. (1991) *PNAS* 88:7978-7982; and McCafferty et al. *Nature* (1990) 348:552-554.

Anti-CD28 antibodies may bind to any portion of the CD28 molecule such that binding of CD28 to CD80 and/or CD86 is modulated upon the binding of the antibody to CD28. Preferably, anti-CD28 antibodies bind to the extracellular domain of the CD28 molecule.

An exemplary anti-CD28 antibody for use in the instant invention is the anti-human CD28 antibody made in a non-human animal, e.g., a rodent. Anti-CD28 antibodies are known in the art, see e.g., U.S. Pat. No. 5,948,893.

Preparation of Anti-CD28 Antibodies

CD28 Immunogens

One aspect of the invention pertains to anti-CD28 antibodies. Antibodies to CD28 can be made by immunizing a subject (e.g., a mammal) with a CD28 polypeptide or a nucleic acid molecule encoding a CD28 polypeptide or a portion thereof. In one embodiment, native CD28 proteins, or immunogenic portions thereof, can be isolated from cells or tissue sources by an appropriate purification scheme using standard protein purification techniques. In another embodiment, CD28 proteins, or immunogenic portions thereof, can be produced by recombinant DNA techniques. Alternative to recombinant expression, a CD28 protein or immunogenic portion thereof, can be synthesized chemically using standard peptide synthesis techniques. Alternatively, nucleic acid molecules encoding a CD28 molecule or portion thereof can be used as immunogens. Whole cells expressing CD28 can be used as immunogens to produce anti-CD28 antibodies.

The origin of the immunogen may be mouse, human, rat, monkey etc. The host animal will generally be a different species than the immunogen, e.g. mouse CD28 used to immunize hamsters, human CD28 to immunize mice, etc. The human and mouse CD28 contain highly conserved stretches in the extracellular domain (Harper et al. (1991) J. Immunol. 147:1037-1044). Peptides derived from such highly conserved regions may be used as immunogens to generate cross-specific antibodies. The nucleotide and amino acid sequences of CD28 from a variety of sources are known in the art and can be found, for example in Proc. Natl. Acad. Sci. U.S.A. 84 (23), 8573-8577 (1987) and J. Immunol. 145:344 (1990); GenBank accession number NM 006139.

In one embodiment, the immunogen may comprise the complete protein, or fragments and derivatives thereof. Preferred immunogens comprise all or a part of the extracellular domain of human CD28 where these residues contain the post-translation modifications, such as glycosylation, found on the native CD28. Immunogens comprising the extracellular domain are produced in a variety of ways known in the art, e.g. expression of cloned genes using conventional recombinant methods, isolation from T cells, sorted cell populations expressing high levels of CD28, etc. In another embodiment, the immunogen may comprise DNA encoding a CD28 molecule or a portion thereof. For example, as set forth in the appended examples, 2 μg cDNA encoding the extracellular domain of recombinant human CD28 could be used as an immunogen.

In a preferred embodiment, the immunogen is a human CD28 molecule. Preferably, CD28 proteins comprise the amino acid sequence encoded by SEQ ID NO:1 or fragment thereof. In another preferred embodiment, the protein comprises the amino acid sequence of SEQ ID NO: 2 or fragment thereof. For example, the CD28 molecule can differ in amino acid sequence from that shown in SEQ ID NO:2, e.g., can be from a different source or can be modified to increase its immunogenicity. In one embodiment, the protein has at least about 80%, and even more preferably, at least about 90% or 95% amino acid identity with the amino acid sequence shown in SEQ ID NO: 2.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The residues at corresponding positions are then compared and when a position in one sequence is occupied by the same residue as the corresponding position in the other sequence, then the molecules are identical at that position. The percent identity between two sequences, therefore, is a function of the number of identical positions shared by two sequences (i.e., % identity=# of identical positions/total # of positions×100). The percent identity between the two sequences is a function of the number of identical positions shared by the sequences, taking into account the number of gaps, and the length of each gap, which need to be introduced for optimal alignment of the two sequences. As used herein amino acid or nucleic acid "identity" is equivalent to amino acid or nucleic acid "homology".

The comparison of sequences and determination of percent identity between two sequences can be accomplished using a mathematical algorithm. In a preferred embodiment, the percent identity between two amino acid sequences is determined using the readily available GAP program in the GCG software package, using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6.

The nucleic acid and protein sequences of the CD28 can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to CD28 nucleic acid molecules of the invention. BLAST protein searches can be performed with the XBLAST program, score=50, wordlength=3 to obtain amino acid sequences homologous to CD28 protein molecules of the invention. To obtain gapped alignments for comparison purposes, Gapped BLAST can be utilized as described in Altschul et al., (1997) *Nucleic Acids Res.* 25(17): 3389-3402. When utilizing BLAST and Gapped BLAST programs, the default parameters of the respective programs (e.g., XBLAST and NBLAST) can be used. See, e.g., the NCBI web page.

CD28 chimeric or fusion proteins or nucleic acid molecules encoding them can also be used as immunogens. As used herein, a CD28 "chimeric protein" or "fusion protein" comprises a CD28 polypeptide operatively linked to a non-CD28 polypeptide. A "CD28 polypeptide" refers to a polypeptide having an amino acid sequence corresponding to CD28 polypeptide, whereas a "non-CD28 polypeptide" refers to a polypeptide having an amino acid sequence corresponding to a protein which is not substantially homologous to the CD28 protein, e.g., a protein which is different from the CD28 protein and which is derived from the same or a different organism. Within a CD28 fusion protein the CD28 polypeptide can correspond to all or a portion of a CD28 protein. In a preferred embodiment, a CD28 fusion protein comprises at least one biologically active portion of a CD28 protein, e.g., an extracellular domain of a CD28 protein. Within the fusion protein, the term "operatively linked" is intended to indicate that the CD28 polypeptide and the non-CD28 polypeptide are fused in-frame to each other. The non-CD28 polypeptide can be fused to the N-terminus or C-terminus of the CD28 polypeptide.

Preferably, a CD28 fusion protein or nucleic acid molecule encoding a CD28 fusion protein is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide or an HA epitope tag). A CD28 encoding nucleic acid molecule can be cloned into such an expression vector such that the fusion moiety is linked in-frame to the CD28 protein. Such fusion moieties can be linked to the C or to the N terminus of the CD28 protein or a portion thereof.

Variants of the CD28 proteins can also be generated by mutagenesis, e.g., discrete point mutation or truncation of a CD28 protein and used as a immunogen. In one embodiment, variants of a CD28 protein can be identified by screening combinatorial libraries of mutants, e.g., truncation mutants, of a CD28 protein for CD28 protein agonist or antagonist activity. In one embodiment, a variegated library of CD28 variants is generated by combinatorial mutagenesis at the nucleic acid level and is encoded by a variegated gene library. A variegated library of CD28 variants can be produced by, for example, enzymatically ligating a mixture of synthetic oligonucleotides into gene sequences such that a degenerate set of potential CD28 sequences is expressible as individual polypeptides, or alternatively, as a set of larger fusion proteins (e.g., for phage display) containing the set of CD28 sequences therein. There are a variety of methods which can be used to produce libraries of potential CD28 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential CD28 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a CD28 protein coding sequence can be used to generate a variegated population of CD28 fragments for screening and subsequent selection of variants of a CD28 protein. In one embodiment, a library of coding sequence fragments can be generated by treating a double stranded PCR fragment of a CD28 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the CD28 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of CD28 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants (Arkin and Yourvan (1992) *Proc. Natl. Acad. Sci. USA* 89:7811-7815; Delgrave et al. (1993) *Protein Engineering* 6(3):327-331).

In one embodiment, cell based assays can be exploited to analyze a variegated CD28 library. For example, a library of expression vectors can be transfected into a cell line which ordinarily synthesizes CD28. The transfected cells are then cultured such that CD28 and a particular mutant CD28 are made and the effect of expression of the mutant on CD28 activity in cell supernatants can be detected, e.g., by any of a number of costimulatory assays. Plasmid DNA can then be recovered from the cells which score for inhibition, or alternatively, potentiation of CD28 activity, and the individual clones further characterized.

An isolated CD28 protein, or a portion or fragment thereof, or nucleic acid molecules encoding a CD28 polypeptide of portion thereof, can be used as an immunogen to generate antibodies that bind CD28 using standard techniques for polyclonal and monoclonal antibody preparation. In one embodiment, a full-length CD28 protein or nucleic acid molecule encoding a full-length CD28 protein can be used. Alternatively, an antigenic peptide fragment (i.e., a fragment capable of promoting an antigenic response) of a CD28 polypeptide or nucleic acid molecule encoding a fragment of a CD28 polypeptide can be used can be used as the immunogen. An antigenic peptide fragment of a CD28 polypeptide typically comprises at least 8 amino acid residues (e.g., at least 8 amino acid residues of the amino acid sequence shown in SEQ ID NO: 2) and encompasses an epitope of a CD28 polypeptide such that an antibody raised against the peptide forms an immune complex with a CD28 molecule. Preferred epitopes encompassed by the antigenic peptide are regions of CD28 that are located on the surface of the protein, e.g., hydrophilic regions. In another embodiment, an antibody binds specifically to a CD28 polypeptide. In a preferred embodiment, the CD28 polypeptide is a human CD28 polypeptide.

Preferably, the antigenic peptide comprises at least about 10 amino acid residues, more preferably at least about 15 amino acid residues, even more preferably at least about 20 amino acid residues, and most preferably at least about 30 amino acid residues. Preferred epitopes encompassed by the antigenic peptide are regions of a CD28 polypeptide that are located on the surface of the protein, e.g., hydrophilic regions, and that are unique to a CD28 polypeptide. In one embodiment such epitopes can be specific for a CD28 proteins from one species, such as mouse or human (i.e., an antigenic peptide that spans a region of a CD28 polypeptide that is not conserved across species is used as immunogen; such non conserved residues can be determined using an amino acid sequence, e.g., using one of the programs described supra). A standard hydrophobicity analysis of the CD28 protein can be performed to identify hydrophilic regions.

A CD28 immunogen can be used to prepare antibodies by immunizing a suitable subject, (e.g., rabbit, goat, mouse or other mammal) with the immunogen. An appropriate immunogenic preparation can contain, for example, a nucleic acid molecule encoding a CD28 immunogen, a recombinantly expressed CD28 protein or a chemically synthesized CD28 immunogen. The preparation can further include an adjuvant, such as Freund's complete or incomplete adjuvant, alum, a cytokine or cytokines, or similar immunostimulatory agent. Immunization of a suitable subject with an immunogenic CD28 preparation induces a polyclonal anti-CD28 antibody response.

Alteration of Antibodies

A variety of different alterations or changes can be introduced into the subject antibodies to optimize their use in downmodulating the immune response. For example, mutations can be introduced into constant and/or variable regions to preserve or enhance e.g., affinity, specificity, and/or half life optionally, alteration may be introduced to decrease immunogenicity. For example, conservative amino acid substitutions can be made. Exemplary changes include: substitution of isoleucine, valine, and leucine for any other of these hydrophoic amino acids. Aspartic acid can be substituted for glutamic acid and vice versa. Glutamine can be substituted for asparagine and vice versa. Serine can be substituted for threonine and vice versa. Other substitutions can also be considered to be conservative, depending on the environment of the particular amino acid and its role in the three-dimensional structure of the protein. For example, glycine and alanine can be interchangeable, as can alanine and valine. Methionine, which is relatively hydrophobic, can often be interchanged with leucine and isoleucine, and sometimes with valine. Lysine and arginine can be interchangeable in locations in which the significant feature of the amino acid residue is its charge and the differing pK's of the two amino acid residues are not significant. Changes that do not affect the three-dimensional structure or the reactivity of the protein can be determined by computer modeling.

For in vivo use, particularly for injection into humans, it is often desirable to decrease the antigenicity of an antibody. An immune response of a recipient against the blocking agent will potentially decrease the period of time that the therapy is effective. To minimize such an immune response, humanized or chimeric antibodies can be constructed. Various methods of humanizing antibodies can be used. For example, the humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) P. N. A. S. 84:3439 and (1987) J. Immunol. 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) Sequences of Proteins of Immunological Interest, N.I.H. publication no. 91-3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Additionally, recombinant anti-CD28 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Patent Publication PCT/US86/02269; Akira, et al. European Patent Application 184, 187; Taniguchi, M., European Patent Application 171,496; Morrison et al. European Patent Application 173,494; Neuberger et al. PCT Application WO 86/01533; Cabilly et al.

U.S. Pat. No. 4,816,567; Cabilly et al. European Patent Application 125,023; Better et al. (1988) *Science* 240:1041-1043; Liu et al. (1987) PNAS 84:3439-3443; Liu et al. (1987) *J. Immunol.* 139:3521-3526; Sun et al. (1987) *PNAS* 84:214-218; Nishimura et al. (1987) *Canc. Res.* 47:999-1005; Wood et al. (1985) *Nature* 314:446-449; and Shaw et al. (1988) *J. Natl Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239: 1534; and Beidler et al. (1988) *J. Immunol.* 141:4053-4060. In addition, humanized antibodies can be made according to standard protocols such as those disclosed in U.S. Pat. Nos. 5,777,085; 5,530,101; 5,693,762; 5,693,761; 5,882,644; 5834597; 5932448; or 5,565,332.

For example, an antibody may be humanized by grafting the desired CDRs onto a human framework, e.g., according to EP-A-0239400. A DNA sequence encoding the desired reshaped antibody can be made beginning with the human DNA whose CDRs it is wished to reshape. The rodent variable domain amino acid sequence containing the desired CDRs is compared to that of the chosen human antibody variable domain sequence. The residues in the human variable domain are marked that need to be changed to the corresponding residue in the rodent to make the human variable region incorporate the rodent CDRs. There may also be residues that need substituting, e.g., adding to or deleting from the human sequence. Oligonucleotides can be synthesized that can be used to mutagenize the human variable domain framework to contain the desired residues. Those oligonucleotides can be of any convenient size.

Alternatively, humanization may be achieved using the recombinant polymerase chain reaction (PCR) methodology taught, e.g., in WO 92/07075. Using this methodology, a CDR may be spliced between the framework regions of a human antibody. In general, the technique of WO 92/07075 can be performed using a template comprising two human framework regions, AB and CD, and between them, the CDR which is to be replaced by a donor CDR. Primers A and B are used to amplify the framework region AB, and primers C and D used to amplify the framework region CD. However, the primers B and C each also contain, at their 5' ends, an additional sequence corresponding to all or at least part of the donor CDR sequence. Primers B and C overlap by a length sufficient to permit annealing of their 5' ends to each other under conditions which allow a PCR to be performed. Thus, the amplified regions AB and CD may undergo gene splicing by overlap extension to produce the humanized product in a single reaction.

Construction of scFv Antigen Binding Portions of Anti-CD28 Antibodies

Single-chain Fv (ScFv) molecules are antigen binding portions in which the VH and VL partner domains are linked via a linker sequence, e.g., an oligopeptide of approximately 15 amino acids such as (Gly4Ser)3, as well as other art recognized linkers. Methods of making scFv molecules are known in the art. (see, e.g., Bird et al (1988) Science 240, 423; Huston et al (1988) Proc. Natl. Acad. Sci, USA 85, 5879; Gilliland et al. 1996. Tissue Antigens. 47:1; Winberg et al. 1996. Immunological Reviews 153:209; Hayden et al. 1996. Tissue Antigens. 48:242).

For example, VL and VH from a hybridoma of interest (e.g., a novel hybridoma made using methods described herein or known in the art or a hybridoma known to produce anti-CD28 antibodies (see, e.g., U.S. Pat. No. 5,948,893) can be cloned and expressed as a scFv protein. mRNA can be isolated from hybridoma cells producing anti-CD28 antibody. Typically, total RNA is isolated by extraction methods well known in the art, such as extraction with phenol at acid pH or extraction with guanidinium thiocyanate followed by centrifugation in cesium chloride solutions or using a commercially available kit (e.g., from Stratagene (Torrey Pines, Calif.). These procedures, and others for RNA extraction, are disclosed in J. Sambrook et al., "Molecular Cloning: A Laboratory Manual" (2d ed., Cold Spring Harbor Laboratory Press, Cold Spring Harbor, N.Y., 1989), ch. 7, "Extraction, Purification, and Analysis of Messenger RNA From Eukaryotic Cells," pp. 7.1-7.25. Optionally, the mRNA can be isolated from the total mRNA by chromatography on oligo (dT) cellulose, but this step is not required.

To synthesize cDNA, primers complementary to the κ or λ light chain constant region and to the constant region of the heavy chain (e.g., γ2a) are preferably used to initiate synthesis. Amplification can be carried out by any procedure allowing high fidelity amplification without slippage. Preferably, amplification is by the polymerase chain reaction procedure (K. B. Mullis & F. A. Faloona, "Specific Synthesis of DNA in vitro Via a Polymerase-Catalyzed Chain Reaction," Meth. Enzymol. 155:335-350 (1987); K. Mullis et al., "Specific Enzymatic Amplification of DNA in vitro: The Polymerase Chain Reaction," Cold Spring Harbor Symp. Quant. Biol. 51:263-273 (1986); R. K. Saiki et al., "Primer-Directed Enzymatic Amplification of DNA with a Thermostable DNA Polymerase," Science 238:487-491 (1988)).

One preferred procedure uses singlesided or anchored PCR (E. Y. Loh et al., "Polymerase Chain Reaction with Single-Sided Specificity: Analysis of T-cell Receptor δ Chain," Science 243:217-220 (1989)). This procedure uses homopolymer tailing of the 3'-end of the reverse transcript; PCR amplification is then performed with a specific 3'-primer and a second oligonucleotide consisting of a homopolymer tail complementary to the homopolymer tail added to the 3'-end of the transcript attached to a sequence with a convenient restriction site, termed the anchor. One version is described in (Y. L. Chiang et al., "Direct cDNA Cloning of the Rearranged Immunoglobulin Variable Region," Biotechniques 7:360-366 (1989)).

The PCR products are cloned into a suitable host, e.g., *E. coli*. A number of cloning vectors suitable for cloning into *E. coli* are known and are described in vol. 1 of Sambrook et al., supra, Ch. 1, "Plasmid Vectors," pp. 1.1-1.110. The exact manipulations required depend on the particular cloning vector chosen and on the particular restriction endonuclease sites used for cloning into the vector. One preferred vector is pUC19. For cloning into pUC19, the PCR products are treated with the Klenow fragment of *E. coli* DNA polymerase I and with the four deoxyribonucleoside triphosphates to obtain blunt ends by filling single-stranded regions at the end of the DNA chains. PCR can then be used to add Eco RI and Bam HI restriction sites to the 5'-end and 3'-ends, respectively, of the amplified fragment of cDNA of light-chain origin (the VL fragment). Similarly, Xba I and Hind III restriction sites are added to the amplified fragment of cDNA of heavy chain origin (the VH fragment). The fragments are digested with the appropriate restriction endonucleases and are cloned into pUC19 vector that had been digested with: (1) Eco RI and Bam HI for VL and (2) Xba I and Hind III for VH. The resulting constructs can be used to transform a competent cell, e.g., an *E. coli* strain.

Clones containing VL and VH are preferably identified by DNA sequencing. A suitable DNA sequencing procedure is the Sanger dideoxynucleotide chain termination procedure. Such a procedure can be performed using the Sequenase 2.0 kit (United States Biochemical, Cleveland, Ohio), with forward and reverse primers that anneal to the pUC19 sequences flanking the polycloning site. Preferably, consensus sequences for VL and VH are determined by comparing the sequences of multiple clones and aligning the sequences with corresponding murine VL and VH variable region sequences (E. A. Kabat et al., "Sequences of Proteins of Immunological Interest" (4th ed., U.S. Department of Health and Human Services, Bethesda, Md., 1987)).

Clones containing VL and VH sequences can be placed in an expression cassette incorporating a single-chain antibody construct including the VL and VH sequences separated by a linker. The expression cassette can be constructed by overlap extension PCR in which the peptide linker between the VL and VH is encoded on the PCR primers. In one highly preferred procedure, the 5'-leader sequence is removed from VL and replaced with a sequence containing a Sal I site preceding residue 1 of the native protein. Constant region residues from the 3'-end are replaced with a primer adding a sequence complementary to a sequence coding for a linker sequence (e.g., the 16-residue linker sequence ESGSVS-SEELAFRSLD (SEQ ID NO:3) [J. K. Batra et al., J. Biol. Chem. 265:15198-15202 (1990)] or [(Gly4Ser)3] Gilliland et al. 1996. Tissue Antigens 47:1].

For the VH sequence, a VH primer adds the "sense" sequence encoding the linker, e.g., the 16-residue linker sequence given above to the VH 5'-end preceding residue 1 of the mature protein and substitutes a sequence complementary to a Bcl I site for the constant region residues at the 3'-end.

The polymerase chain reaction can then be used with a mixture of VL and VH cDNA, as templates, and a mixture of the four primers (two linker primers and two primers containing restriction sites). This creates a single DNA fragment containing a VL-linker-VH sequence flanked by Sal I and Bcl I sites. The DNA construct is then preferably passaged through, e.g., E. coli cells. The passaged construct is then digested with Sal I and Bcl I.

For preparation and expression of the fusion protein, digested DNA from the preceding step is then ligated into a pCDM8 vector containing the anti-CD28 light chain leader sequence followed by a Sal I site and a Bcl I site preceding cDNA encoding, e.g, a human or humanized Ig tail (e.g., IgG) in which cysteines in the hinge region are mutated to serines to inhibit dimerization (P. S. Linsley et al., "Binding of the B Cell Activation Antigen B7 to CD28 Costimulates T-Cell Proliferation and Interleukin-2 mRNA Accumulation," J. Exp. Med. 191:721-730 (1991) or another peptide molecule (Gilliland et al. 1996. Tissue Antigens 47:1).

The resulting construct is capable of expressing anti-CD28 scFv antibody. Exemplary constructs comprise non-human (e.g., murine) CDRs and human constant regions. The constructs can be placed in a vector, e.g., a plasmid.

Plasmid DNA can then isolated and purified, such as by cesium chloride density gradient centrifugation. The purified DNA is then transfected, e.g., into a prokaryotic cell or eukaryotic cell, using methods that are known in the art. A highly preferred cell line is monkey COS cells. A preferred method of introducing DNA is by DEAE-dextran, but other methods are known in the art. These methods include contacting a cell with coprecipitates of calcium phosphate and DNA, use of a polycation, polybrene, or electroporation. These methods are described in J. Sambrook et al., "Molecular Cloning: A Laboratory Manual," supra, vol. 3, pp. 16.30-16.55.

Preferably, recombinant DNA containing the sequence coding for the fusion protein is expressed by transient expression, as described in A. Aruffo, "Transient Expression of Proteins Using COS Cells," in Current Protocols in Molecular Biology (2d ed., F. M. Ausubel et al., eds., John Wiley & Sons, New York, 1991), pp. 16.13.1-16.13.7.

B. Other Agents

In addition to antibodies which bind to CD28, other agents known in the art can also be used to inhibit activation of CD28 and thus block CD28-mediated signaling. Any agent which binds to CD28 to effectively block ligand binding, without itself activating the CD28 receptor (e.g., via aggregation of the receptor) will effectively block CD28-mediated signaling. Alternatively, any agent which binds to a ligand(s) of CD28 to prevent binding and activation of CD28 will also block CD28-mediated signaling. A variety of such agents are know in the art.

Exemplary Agents

One such agent which will bind to CD28 without triggering activation is a soluble form of ligand which is in monomeric form. A soluble form of a CD28 ligand may contain an amino acid sequence corresponding to the extracellular domain of the ligand protein or any fragment thereof which does not include the cytoplasmic and/or transmembrane regions. Alternatively, the soluble form may contains a smaller region which is involved in CD28 binding. Such polypeptides, when produced recombinantly in a host cell, will be secreted freely into the medium, rather than anchored in the membrane. It is critical that the soluble form of the ligand be in monomeric form, so as not to cross link the CD28 molecule, and thus activate CD28-mediated signaling.

In one embodiment, the soluble ligand of CD28 is derived from a naturally occurring B7 molecule (e.g., B7-1, B7-2 or B7-3). DNA sequences encoding B7 proteins are known in the art, see e.g., B7-2 (Freeman et al. 1993 Science. 262:909 or GenBank Accession numbers P42081 or A48754); B7-1 (Freeman et al. J. Exp. Med. 1991. 174:625 or GenBank Accession numbers P33681 or A45803. The extracellular portion of the ligand (e.g., approximately amino acid residues 1-208 of the sequence of B7-1 or approximately amino acids 24-245 of the sequence of B7-2), or a fragment thereof which is sufficient for CD28 binding is used to generate the soluble ligand. It may further be useful to express the portion or fragment of the ligand as a fusion protein. Polypeptides having binding activity (e.g., binding to CD28) of a B7 molecule, and having a sequence which differs from a naturally occurring B7 molecule due to degeneracy in the genetic code, can also be expressed in soluble form and are also within the scope of the invention. Such polypeptides are functionally equivalent to B7, (e.g., a polypeptide having B7 activity) but differ in sequence from the sequence of B7 molecules known in the art. It will be appreciated by one skilled in the art that these variations in one or more nucleotides (up to about 3-4% of the nucleotides) of the nucleic acids encoding peptides having the activity of a novel B lymphocyte antigen may exist among individuals within a population due to natural allelic variation. Such nucleotide variations and resulting amino acid polymorphisms are also within the scope of the invention. Furthermore, there may be one or more isoforms or related, cross-reacting B7 molecules.

By way of example, to express a secreted (soluble) form of the B7-1 polypeptide comprising amino acids 1-212, a PCR product may be synthesized using the following two oligonucleotide primers and the B7-1 cDNA clone: (1) a sense primer consisting of a restriction enzyme site and 20 nucleotides corresponding to the translational initiation site and the first few amino acid codons of B7-1, and (2) an anti-sense primer consisting of 20 nucleotides corresponding to the last few amino acid codons of B7-1 ending at codon 212, (i.e., before the transmembrane region) followed by a stop codon and a restriction enzyme site. The PCR product may then be digested with the restriction endonuclease whose recognition sequence is in the PCR primers, gel purified, eluted, and ligated into an appropriate expression vector. The expression construct may then be introduced into a eukaryotic cell such as Cos7, where the B7-1 polypeptide fragment is synthesized and secreted. The B7-1 polypeptide fragment thus produced can then readily be obtained from the culture media. Such a soluble form of B7-1 was produced in U.S. Pat. No. 6,071,716, the contents of which are incorporated herein by reference.

Another exemplary agent which will bind to CD28 to block CD28-mediated signaling is a peptidomimetic or a small molecule.

Peptide analogs are commonly used in the pharmaceutical industry as non-peptide drugs with properties analogous to those of the template peptide. These types of non-peptide compound are termed "peptide mimetics" or "peptidomimetics" (Fauchere, J. (1986) *Adv. Drug Res.* 15:29; Veber and Freidinger (1985) TINS p. 392; and Evans et al. (1987) *J. Med. Chem.* 30:1229, which are incorporated herein by reference) and are usually developed with the aid of computerized molecular modeling. Peptide mimetics that are structurally similar to CD28, CD28 ligands, or functional variants thereof, can be used to produce an equivalent product to the blocking agents described above. Generally, peptidomimetics are structurally similar to the paradigm polypeptide but have one or more peptide linkages optionally replaced by a linkage selected from the group consisting of: —CH2NH—, —CH2S—, —CH2—CH2—, —CH=CH— (cis and trans), —COCH2—, —CH(OH)CH2—, and —CH2SO—. This is accomplished by the skilled practitioner by methods known in the art which are further described in the following references: Spatola, A. F. in "*Chemistry and Biochemistry of Amino Acids, Peptides, and Proteins*" Weinstein, B., ed., Marcel Dekker, New York, p. 267 (1983); Spatola, A. F., Vega Data (March 1983), Vol. 1, Issue 3, "Peptide Backbone Modifications" (general review); Morley, J. S. (1980) *Trends Pharm. Sci.* pp. 463-468 (general review); Hudson, D. et al. (1979) *Int. J. Pept. Prot. Res.* 14:177-185 (—CH2NH—, CH2CH2—); Spatola, A. F. et al. (1986) *Life Sci.* 38:1243-1249 (—CH2—S); Hann, M. M. (1982) *J. Chem. Soc. Perkin Trans. I.* 307-314 (—CH—CH—, cis and trans); Almquist, R. G. et al. (190) *J. Med. Chem.* 23:1392-1398 (—COCH2—); Jennings-White, C. et al. (1982) *Tetrahedron Lett.* 23:2533 (—COCH2—); Szelke, M. et al. European Appln. EP 45665 (1982) CA: 97:39405 (1982)(—CH(OH)CH2—); Holladay, M. W. et al. (1983) *Tetrahedron Lett.* (1983) 24:4401-4404 (—C(OH)CH2—); and Hruby, V. J. (1982) *Life Sci.* (1982) 31:189-199 (—CH2—S—); each of which is incorporated herein by reference. A particularly preferred non-peptide linkage is —CH2NH—. Such peptide mimetics may have significant advantages over polypeptides, including, for example: more economical production, greater chemical stability, enhanced pharmacological properties (half-life, absorption, potency, efficacy, etc.), altered specificity (e.g., a broad-spectrum of biological activities), and reduced antigenicity.

For example, peptidomimetics may be specifically designed from information about potential contact surfaces of the CD28 molecule with its ligand, or regions of the CD28 molecule responsible for mediating homodimer formation in order to disrupt the appropriate presentation of the homodimers. Such an approach was used by El Tayar et al., (WO 98/56401 (1998)), the contents of which are incorporated herein by reference, in the design of peptidomimetics which inhibit CD28 mediated signaling.

The term "small molecule" is a term of art and included molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, nucleic acids, carbohydrates, small organic molecules (e.g., polyketides) (Cane et al. 1998. Science 282:63), and natural product extract libraries. In another embodiment, the compounds are small, organic non-peptidic compounds. In a further embodiment, a small molecule is not biosynthetic.

A number of agents which bind to the CD28 ligand to prevent CD28 binding and thus block CD28-mediated signaling are known in the art. One such agent is a soluble form of CD28. A soluble form of CD28 is usually made of the extracellular portion of the receptor, or a fragment thereof which retains the ability to bind to the ligand. In one embodiment, the portion or fragment of the receptor is produced in the form of a fusion protein, e.g., an Ig fusion protein. One such soluble form of a CD28 molecule has been used to block the transduction of a costimulatory signal in a T cell (see e.g., U.S. Pat. No. 5,521,288).

In addition, a soluble form of a receptor which binds to a CD28 ligand (e.g., CTLA4 or ICOS) will also prevent ligand binding of CD28 to block CD28-mediated signaling. Such soluble forms of these cell surface molecules have been found to block the transduction of a costimulatory signal in a T cell. In one embodiment, a soluble form of a CD28 or ICOS molecule can be used to block the transduction of a costimulatory signal in a T cell (see e.g., U.S. Pat. No. 5,521,288).

In one embodiment, the agent which blocks CD28-mediated signaling is a soluble form of CTLA4. DNA sequences encoding the human and murine CTLA4 protein are known in the art, see e.g., Dariavich, et al. (1988) *Eur. J Immunol.* 18(12), 1901-1905; Brunet, J. F., et al. (1987) supra; Brunet, J. F. et al. (1988) *Immunol. Rev.* 103:21-36; and Freeman, G. J., et al. (1992) *J. Immunol.* 149, 3795-3801. In certain embodiments, the soluble CTLA4 protein comprises the entire CTLA4 protein. In preferred embodiments, a soluble CTLA4 protein comprises the extracellular domain of a CTLA4 protein. For example, a soluble, recombinant form of the extracellular domain of CTLA4 has been expressed in yeast (Gerstmayer et al. 1997. *FEBS Lett.* 407:63). In other embodiments, the soluble CTLA4 proteins comprise at least a portion of the extracellular domain of CTLA4 protein which retains the ability to bind to B7-1 and/or B7-2.

In one embodiment the soluble CTLA4 protein or portion thereof is a fusion protein comprising at least a portion of CTLA4 which binds to B7-1 and/or B7-2 and at least a portion of a second non-CTLA4 protein. For example, a soluble, recombinant form of the extracellular domain of CTLA4 has been expressed in yeast (Gerstmayer et al. 1997. *FEBS Lett.* 407:63). In preferred embodiments, the CTLA4 fusion protein comprises a CTLA4 extracellular domain which is fused at the amino terminus to a signal peptide, e.g., from oncostatin M (see e.g., WO93/00431).

In a particularly preferred embodiment, a soluble form of CTLA4 is a fusion protein comprising the extracellular domain of CTLA4 fused to a portion of an immunoglobulin molecule. Such a fusion protein, CTLA4Ig, can be made using methods known in the art (see e.g., Linsley 1994. *Perspectives in Drug Discovery and Design* 2:221; Linsley WO 93/00431 and U.S. Pat. Nos. 5,770,197, and 5,844,095).

Antibodies which bind to a CD28 ligand to prevent CD28 binding also block CD28-mediated signaling. In one embodiment, antibodies for use in the instant methods bind to at least one B7 molecule. In yet another embodiment, an antibody of the invention binds to only one B7 molecule (e.g., to B7-1 and not to B7-2). Such antibodies are known in the art. For example, The 2D10 hybridoma, producing the 2D10 antibody, has been described (Journal of Immunology. 1994. 152:2105). In addition, for use in combination with an anti-B7-2 antibody, several anti-B7-1 antibodies are known or are readily available (see, e.g., U.S. Pat. No. 5,869,050; Powers G. D., et al. (1994) *Cell. Immunol.* 153, 298-311; Freedman, A. S. et al. (1987) *J. Immunol.* 137:3260-3267; Freeman, G. J. et al. (1989) *J. Immunol.* 143:2714-2722; Freeman, G. J. et al. (1991) *J. Exp. Med.* 174:625-631; Freeman, G. J. et al. (1993) *Science* 262:909-911; WO 96/40915). Such antibodies are also commercially available, e.g., from R&D Systems (Minneapolis, Minn.) and from Research Diagnostics (Flanders, N.J.). Antibodies to B7-2 known in the art are, for example, anti-human B7-2 monoclonal antibodies produced by hybridomas HA3.1F9, HA5.2B7 and HF2.3D1. Monoclonal antibody HA3.1F9 is of the IgG1 isotype; monoclonal antibody HA5.2B7 is of the IgG2b isotype; and monoclonal antibody HF2.3D1 is of the IgG2a isotype. The preparation and characterization of these antibodies is described in detail in U.S. Pat. No. 6,084,067 (2000), the contents of which are incorporated herein by reference.

To generate antibodies to a ligand of CD28, such as a B7 protein (e.g., B7-1, B7-2 or B7-3) full-length B7 protein, or a peptide fragment thereof, having an amino acid sequence based on the predicted amino acid sequence of the B7 protein, anti-protein/anti-peptide polyclonal antisera or monoclonal antibodies can be made using standard methods, described above. A mammal, (e.g., a mouse, hamster, or rabbit) can be immunized with an immunogenic form of the protein or peptide which elicits an antibody response in the mammal. The immunogen can be, for example, a recombinant B7 protein, or fragment thereof, a synthetic peptide fragment or a cell that expresses a B lymphocyte antigen on its surface. The cell can be for example, a splenic B cell or a cell transfected with a nucleic acid molecule encoding a B lymphocyte antigen such that the B lymphocyte antigen is expressed on the cell surface. The immunogen can be modified to increase its immunogenicity. For example, techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay can be used with the immunogen as antigen to assess the levels of antibodies.

Screening Assays to Identify Novel Agents

A number of screening assays for identifying an agent (e.g., antibodies, peptides, peptidomimetics, small molecules or other drugs) that blocks CD28-mediated signaling are available in the art. Generally speaking, the agent is identified from one or more test agents (also referred to herein as candidate or test compounds) which are assayed for the ability block CD28-mediated signaling with a standard in vitro assay for immune response wherein CD28-mediated signaling, and thus the immune response, is downregulated by the presence of the functional agent. A number of suitable readouts of immune cell activation (e.g., cell proliferation or effector function such as antibody production, cytokine production, and phagocytosis) in the presence of the agent exist in the art. One commonly used assay is a T cell activation assay.

Typically, the chosen assay is manipulated by standard methods to induce an immune response via CD28-mediated signaling, in the presence or absence of a test agent. A comparative reduction in the CD28-mediated signaling, e.g., a reduction in the induction of the immune response, in the presence of the test agent indicates the test agent blocks CD28-mediated signaling. Inhibition of CD28-mediated signaling, as detected, e.g., by downregulation of the immune response results in a statistically significant and reproducible decrease in the immune response or downregulation of T cell activation preferably as measured by the assay. Agents that block CD28-mediated signaling can be identified by their ability to inhibit immune cell proliferation and/or effector function or to induce anergy when added to such an in vitro assay.

For example, immune cells are cultured in the presence of an agent that stimulates signal transduction via CD28. A readout of cell activation can be employed to measure cell proliferation or effector function (e.g., antibody production, cytokine production, phagocytosis) in the presence of the activating agent, a number of such readouts are known in the art. The ability of an agent to block cell activation can be readily determined by measuring the ability of the agent to affect a decrease in proliferation or effector function. A method for the identification of such agents is discussed in more detail below.

The test compound of the present invention can be, for instance, any of the compounds described above. In one embodiment, the compound is an agent not previously known to inhibit CD-28-mediated signaling. In another embodiment, a plurality of compounds are tested. Such compounds may be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc. Natl. Acad. Sci. USA* 89:1865-1869) or on phage (Scott and Smith (1990) *Science* 249:386-390); (Devlin (1990) *Science* 249:404-406); (Cwirla et al. (1990) *Proc. Natl. Acad. Sci. USA* 87:6378-6382); (Felici (1991) *J. Mol. Biol.* 222:301-310); (Ladner supra).

In another embodiment, an assay is a cell-based assay comprising contacting a cell expressing a CD28 with a test compound and determining the ability of the test compound to inhibit or block the activity of CD28 with respect to induced signaling. Determining the ability of the test compound to block CD28 induced signaling can be accomplished, for example, by determining the ability of CD28 to bind to or interact with its natural ligands. Determining the ability of CD28 to bind to or interact with its natural ligand can be accomplished, for instance by measuring direct binding, or by detection of CD28-mediated signaling.

In a direct binding assay, the CD28 protein, or a modified version or mimetic thereof (or their respective receptors) can be coupled with a radioisotope or enzymatic label such that binding of the CD28 protein to a target molecule can be determined by detecting the labeled protein in a complex. For example, CD28 molecules, can be labeled with $^{125}$I, $^{35}$S, $^{14}$C, or $^{3}$H, either directly or indirectly, and the radioisotope detected by direct counting of radioemmission or by scintillation counting. Alternatively, CD28 molecules can be enzymatically labeled with, for example, horseradish peroxidase, alkaline phosphatase, or luciferase, and the enzymatic label detected by determination of conversion of an appropriate substrate to product.

A test agent or compound may function to block CD28-mediated signaling by inhibiting the interaction between CD28 and its ligand. Such an activity of a test agent or compound to modulate the interaction between CD28 and its ligand can be determined without the labeling of any of the interactants. For example, a microphysiometer can be used to detect the interaction of CD28 with its ligand without the labeling of either CD28 or the ligand (McConnell, H. M. et al. (1992) *Science* 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, determining the ability of a test agent to block CD28-mediated signaling can be accomplished by determining the activity of a ligand of CD28 at inducing signaling via CD28 in the presence of the test agent. CD28-mediated signaling can be determined, for instance, by detecting induction of a cellular second messenger (e.g., tyrosine kinase activity), detecting catalytic/enzymatic activity of an appropriate substrate, detecting the induction of a reporter gene (comprising a target-responsive regulatory element operatively linked to a nucleic acid encoding a detectable marker, e.g., chloramphenicol acetyl transferase), or detecting another cellular response regulated by CD28.

In another embodiment, the assay is a cell-free assay in which a CD28 molecule is contacted with a test agent and the ability of the test agent to inhibit the activity of a CD28 ligand or biologically active portion thereof (at inducing signaling via CD28) is determined. This can be accomplished, for example, by determining the ability of the ligand to bind CD28, e.g., using a technology such as real-time Biomolecular Interaction Analysis (BIA) (Sjolander, S. and Urbaniczky, C. (1991) *Anal. Chem.* 63:2338-2345 and Szabo et al. (1995) *Curr. Opin. Struct. Biol.* 5:699-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

III. Pharmaceutical Compositions

The active molecules of the invention (e.g., antigen binding portions of anti-CD28 antibodies or small molecules) can be suspended in a any known physiologically compatible pharmaceutical carrier, such as cell culture medium, physiological saline, phosphate-buffered saline, or the like, to form a physiologically acceptable, aqueous pharmaceutical composition. Parenteral vehicles include sodium chloride solution, Ringer's dextrose, dextrose and sodium chloride, and lactated Ringer's. Other substances may be added as desired such as antimicrobials.

An active molecule for downmodulating the immune response can be incorporated into a composition, e.g., a pharmaceutical composition suitable for administration. Such compositions typically further comprise a carrier, e.g., a pharmaceutically acceptable carrier. As used herein the language "carrier" is intended to include any and all solvents, dispersion media, coatings, antibacterial and antifungal agents, isotonic and absorption delaying agents, and the like, compatible for use with cells, e.g., compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions can be included in a container, pack, or dispenser together with instructions for administration. The kit can further comprise a means for administering the active molecule of the invention, e.g., one or more syringes. The kit can come packaged with instructions for use.

IV. Uses and Methods of the Invention

The active molecules of the invention are useful in downmodulating the immune response. The present invention provides for both prophylactic and therapeutic methods of treating a subject at risk of (or susceptible to) a disorder or having a disorder associated with an aberrant or undesirable immune response, e.g., autoimmune diseases, allergy and allergic reactions, transplantation rejection, and established graft versus host disease in a subject.

The active molecules of the invention can be used to downmodualte both primary and secondary immune responses. They can be used to downmodulate immune responses mediated, either directly or indirectly (e.g., based on helper function) by T cells. In one embodiment, the subject compositions and methods are used to downmodulate CD4+ T cell responses. In another embodiment, the subject compositions and methods are used to downmodulate CD8+ T cell responses.

In one aspect, the invention provides a method for preventing an undesirable immune response in a subject. Administration of an active molecule of the invention can occur prior to the manifestation of symptoms for which modulation of the immune response would be beneficial, such that a disease or disorder is prevented or, alternatively, delayed in its progression. Such administration can be used to prevent or downmodulate primary immune responses. Another aspect of the invention pertains to methods of modulating an immune response for therapeutic purposes, e.g., to downmodulate ongoing or secondary immune responses.

The present invention provides methods of treating a subject afflicted with a disease or disorder that would benefit from downmodulation of the immune response by contacting cells from the subject with an agent that specifically binds to CD28. An agent that specifically binds to CD28 can be administered ex vivo (e.g., by contacting the cell with the agent in vitro) or, alternatively, in vivo (e.g., by administering the agent to a subject). Likewise, a cell can be made to express an agent that specifically binds to CD28 either in vivo or ex vivo.

Downmodulation of the immune response is useful to downmodulate the immune response, e.g., in situations of tissue, skin and organ transplantation, in graft-versus-host disease (GVHD), allergy, or in autoimmune diseases. Autoimmune diseases that will benefit from the instant methods include those mediated by humoral and/or cellular mechanisms. Exemplary autoimmune diseases or disorders include, but are not limited to: systemic lupus erythematosus, diabetes mellitus (e.g., autoimmune diabetes or type I diabetes), rheumatoid arthritis, multiple sclerosis, myasthenia gravis, systemic lupus enthmatosus, and autoimmune thyroiditis, vitiligo, alopecia, celiac disease, inflammatory bowel disease, chronic active hepatitis, Addison's disease, Hashimoto's disease, Graves disease, atrophic gastritis/pernicious anemia, acquired hypogonadism/infertility, hypoparathyroidism, Myasthenia gravis, Coombs positive hemolytic anemia, chronic allergic diseases (such as asthma, hay fever, or allergic rhinitis), and Sjogren's syndrome.

For example, blockage of immune responses results in reduced tissue destruction in tissue transplantation. Typically, in tissue transplants, rejection of the transplant is initiated through its recognition as foreign by immune cells, followed by an immune reaction that destroys the transplant. The administration of an active molecule of the invention prior to or at the time of transplantation, can inhibit the immune response. In one embodiment, a cell for transplantation is caused to express a soluble form of an agent that specifically binds to CD28.

In one embodiment, use of the active molecules of the invention is sufficient to anergize the immune cells, thereby inducing tolerance in a subject. In another embodiment, the active molecules of the invention are administered repeatedly (i.e., more than once) to achieve optimal reduction in one or more immune response(s). In one embodiment, long term tolerance is induced in a subject and may avoid the necessity of repeated administration of these blocking reagents.

To achieve sufficient immunosuppression or tolerance in a subject, it may also be desirable to block the costimulatory function of other molecules. For example, it may be desirable to block the function of B7-1, B7-2, or B7-1 and B7-2 by administering a soluble form of a combination of peptides having an activity of each of these antigens or blocking antibodies against these antigens (separately or together in a single composition) prior to or at the time of transplantation. Other downmodulatory agents that can be used in connection with the downmodulatory methods of the invention include, for example, blocking antibodies against other immune cell markers or soluble forms of other receptor ligand pairs (e.g., agents that disrupt the interaction between CD40 and CD40 ligand (e.g., anti CD40 ligand antibodies)), antibodies against cytokines, fusion proteins (e.g., CTLA4-Fc), and/or immunosuppressive drugs, (e.g., rapamycin, cyclosporine A or FK506).

The active molecules of the invention are also useful in treating autoimmune disease. Many autoimmune disorders are the result of inappropriate activation of immune cells that are reactive against self tissue and which promote the production of cytokines and autoantibodies involved in the pathology of the diseases. Preventing the activation of autoreactive immune cells may reduce or eliminate disease symptoms. The active molecules of the invention are useful to inhibit immune cell activation and prevent production of autoantibodies or cytokines which may be involved in the disease process.

Inhibition of immune cell activation can also be used therapeutically in the treatment of allergy and allergic reactions, e.g., by inhibiting IgE production. An active molecule of the invention can be administered to an allergic subject to inhibit immune cell mediated allergic responses in the subject. Administration of an active compound can be accompanied by exposure to allergen. Allergic reactions can be systemic or local in nature, depending on the route of entry of the allergen and the pattern of deposition of IgE on mast cells or basophils. Thus, inhibition of immune cell mediated allergic responses can be effected locally or systemically by administration of an active molecule of the invention.

VI. Administration of Active Molecules of the Invention

The active molecules of the invention may be introduced into the subject to be treated by using one of a number of methods of administration of therapeutics known in the art. For example, active molecules may be administered parenterally (including, for example, intravenous, intraperitoneal, intramuscular, intradermal, and subcutaneous), by ingestion, or applied to mucosal surfaces. Alternatively, the active molecules of the invention are administered locally by direct injection at the site of an ongoing immune response.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition will be sterile and should be fluid to the extent that easy syringability exists. A composition will be stable under the conditions of manufacture and storage and are preferably preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Active molecules of the invention can be introduced into a subject with an antigen or antigens corresponding to those to which an immune response to be downmodulated is directed. Such molecules can be introduced into a subject prior to onset of an immune response or when an immune response is ongoing.

A "therapeutically effective amount" of a composition of the invention is a dose sufficient to reduce or suppress an immune response to the selected antigen.

Routes of administration include epidermal administration including subcutaneous or intradermal injections. Transdermal transmission including iontophoresis may be used, for example "patches" that deliver product continuously over periods of time.

Mucosal administration of the active molecules of the invention is also provided for, including intranasal administration with inhalation of aerosol suspensions. Suppositories and topical preparations may also be used. The dosage of a sufficient amount or number of the active molecules to downmodulate T response(s) in a subject can be readily determined by one of ordinary skill in the art. The active molecules may be introduced in at least one dose and either in that one dose or through cumulative doses are effective in reducing an immune response. The active molecules are administered in a single infusion or in multiple, sequential infusions.

Different subjects are expected to vary in responsiveness to such treatment. Dosages will vary depending on such factors as the individual's age, weight, height, sex, general medical condition, previous medical history, and immune status. Therefore, the amount or number of active molecules infused as well as the number and timing of subsequent infusions, is determined by a medical professional carrying out the therapy based on the response of the patient.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

After administration, the efficacy of the therapy can be assessed by a number of methods, such as assays that measure T cell proliferation, T cell cytotoxicity, antibody production, and/or clinical response. An decrease in the production of antibodies or immune cells recognizing the selected antigen will indicate a downmodulated immune response. Efficacy may also be indicated by improvement in or resolution of the disease (pathologic effects), associated with the reduction or disappearance of the unwanted immune response, or improvement in or resolution of the disease (pathologic effects) associated with the unwanted immune response (e.g. autoimmune disease) allergic reaction or transplant rejection). For example, standard methodologies can be used to assay, e.g., T cell proliferation, cytokine production, numbers of activated T cells, antibody production, or delayed type hypersensitivity. In addition or alternatively, improvement in a specific condition for which treatment is being given can be monitored, e.g., insulin levels can be monitored in a subject being treated for diabetes.

The practice of the present invention employs conventional techniques of molecular biology, microbiology, recombinant DNA, and immunology, within the skill of these arts. Such techniques are found in the scientific literature (See, e.g., Brock, Biology of Microorganisms, Eighth Ed., (1997), (Madigan et al., eds.), Prentice Hall, Upper Saddle River, N.J.; Sambrook et al., Molecular Cloning: A Laboratory Manual, Second Ed., (1989); Oligonucleotide Synthesis, M. J. Gait Ed., 1984, Animal Cell Culture, Freshney, ed., 1987; Methods in Enzymology, series, Academic Press, Inc.; Gene Transfer Vectors for Mammalian Cells, Miller and Calos, Eds., 1987; Handbook of Experimental Immunology, Weir and Blackwell, Eds., Current Protocols in Molecular Biology. Ausubel et al, Eds., 1987, and Current Protocols in Immunology, Coligan et al., Eds., 1991). These references are incorporated in their entirety herein by reference.

This invention is further illustrated by the following examples which should not be construed as limiting. The contents of all references, patents and published patent applications cited throughout this application, as well as the Figures and the Sequence Listing are incorporated herein by reference.

EXAMPLES

The NOD mouse model for diabetes was used in these examples. The NOD mouse undergoes an autoimmune destruction of pancreatic islet B cells similar to that seen in patients with human type I diabetes. Infiltration of CD4+ and CD8+ T cells into the Islets of Langerhans begins at 4-5 weeks of age. These Examples show that, in contrast to whole anti-CD28 antibody PV1 (also referred to herein as PV1.10.17, as described in U.S. Pat. No. 5,948,893), PV1-scFv surprisingly prevents disease onset in both weanling NOD as well as adult female NOD mice.

Example 1

Anti-CD28 (PV1) and PV1-scFv Bind to CD28 Equally

BIAcore experiments have been done comparing the binding of PV1, PV1-scFV, mCD28. Fc (murine CD28 fused to IgG Fc domain) and mIgG2A (murine IgG2A) to murine CD28 (mCD28. Fc), which show that PV1-scFv and anti-CD28 (PV1.10.17) bind equally well to murine CD28 (FIG. 1).

Example 2

PV1-scFv Inhibits T Cell Responses In Vitro

Figure 2:
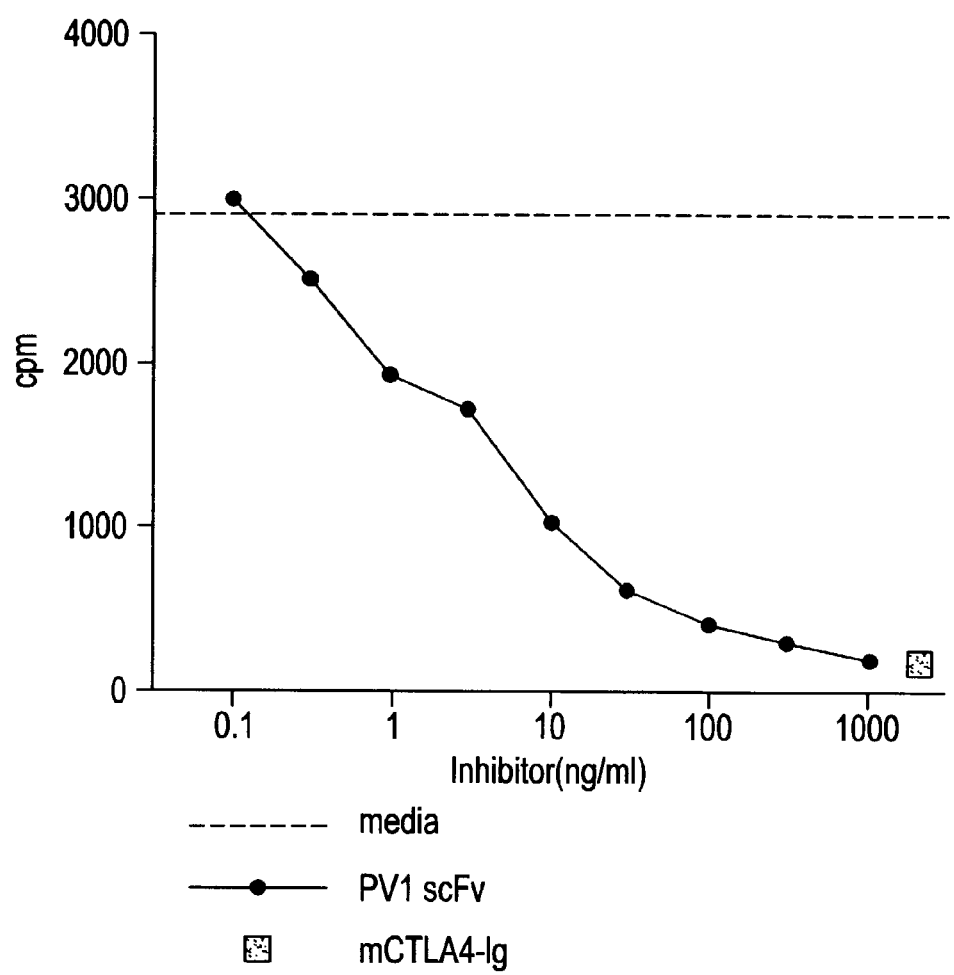
FIG. 2 shows that PV1 (anti-CD28) scFv inhibits T cell responses in vitro.

PV1-scFv blocks costimulation of anti-CD3 responses in vitro (FIG. 2). In this example, $1\times10^5$ NOD spleen cells were cultured with 1 µg/ml anti-CD3. PV1-scFv or mCTLA4-Ig were added on day 0. Proliferation (cpm of $^3$H-thymidine incorporated into the DNA of the cells) was measured on day 3.

Example 3

PV1-scFv Delays Disease Onset in Two Week Old NOD Female Mice

Figure 3:
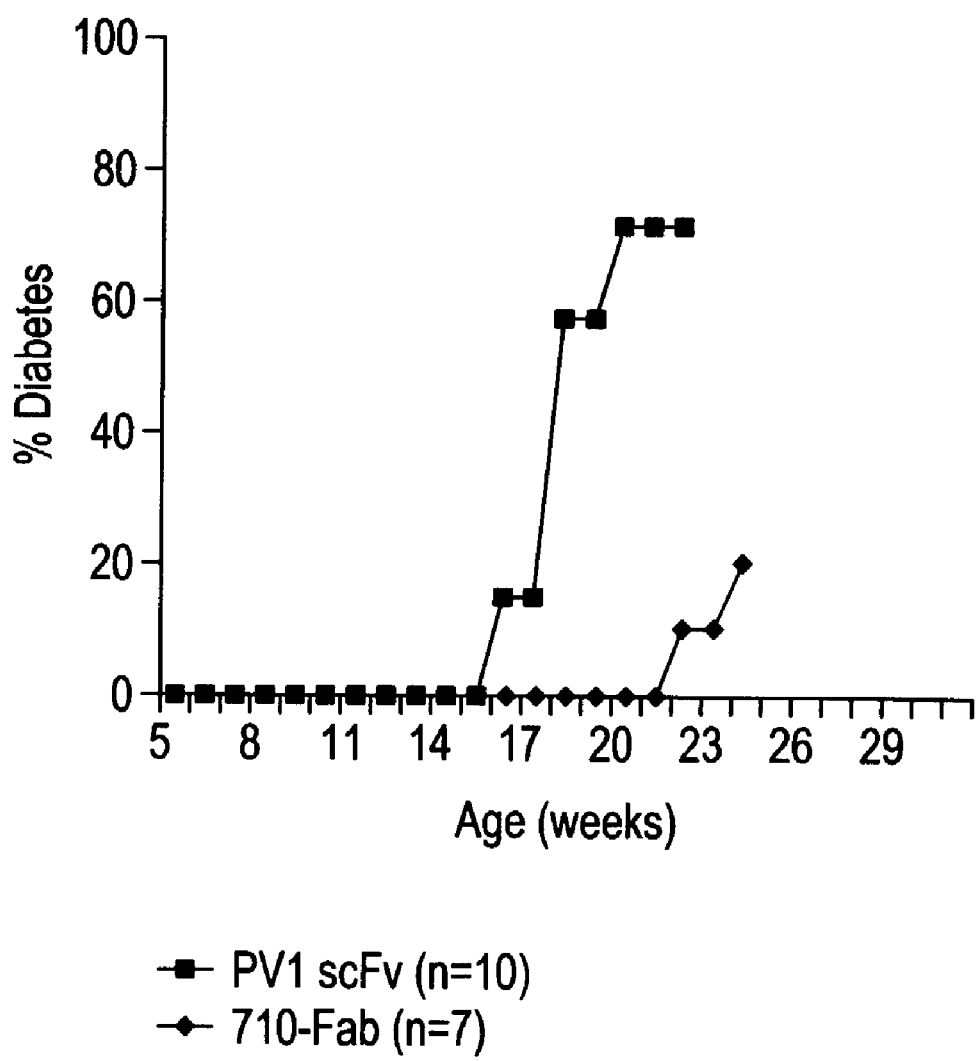
FIG. 3 shows that PV1 (anti-CD28) scFv delays disease onset in two week old NOD female mice.

Two to three week old female NOD mice were injected with 50 µg PV1-scFv every other day for two weeks with an additional dose at five, six, and seven weeks. At 27 weeks of age, only 20% of the PV1-scFv treated mice were diabetic, in contrast, 80% of control mice were diabetic (FIG. 3). In this example, 50 µg PV1-scFv or 710-Fab, was administered to 2 week old female NOD mice every other day for 14 days with an additional dose at 5, 6, and 7 weeks.

Example 4

PV1-scFv Delays Disease Onset in Adult (8 Week Old) NOD Female Mice

Figure 4:
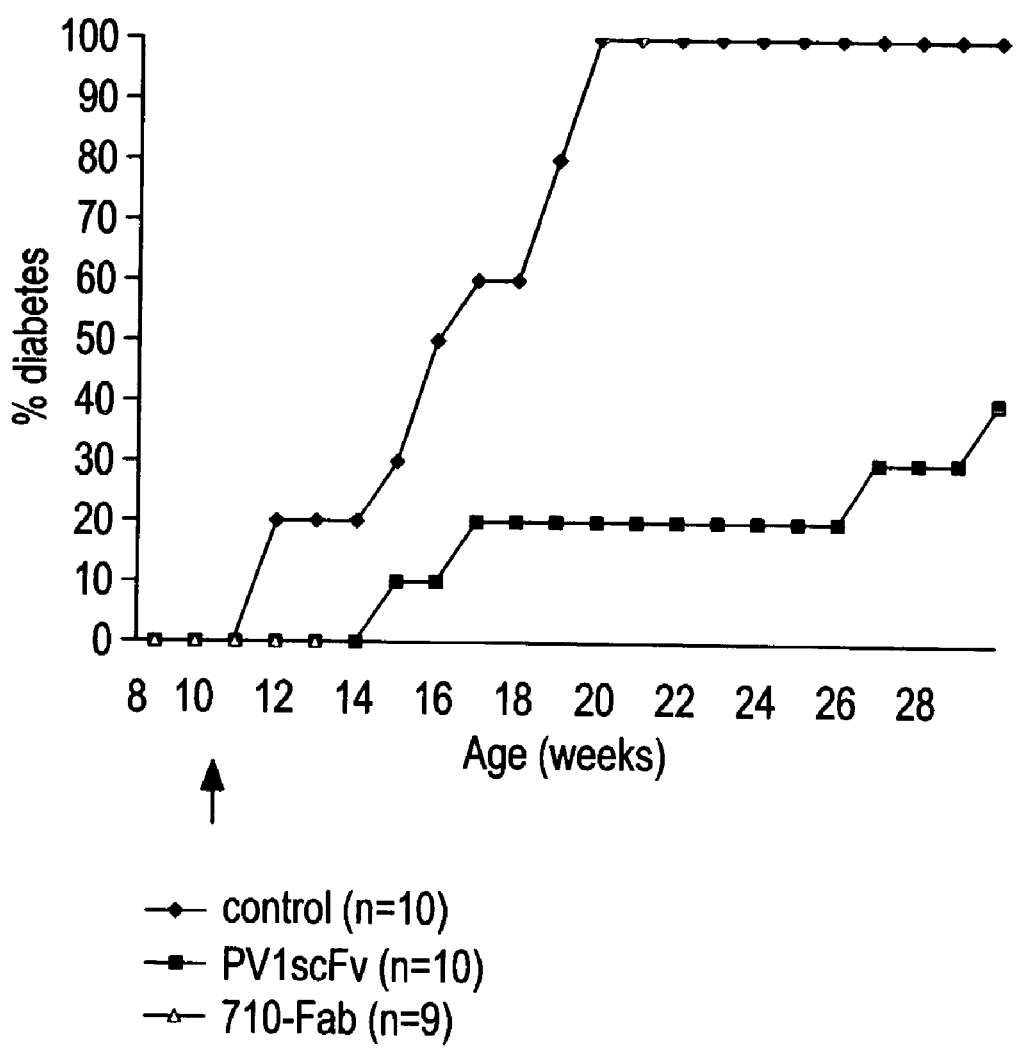
FIG. 4 shows that PV1 scFv delays disease onset in adult (8 week old) NOD female mice.

Adult female NOD mice were injected with 50 µg PV1-scFv daily from eight to ten weeks. At thirty weeks of age, only 40% of the PV1-scFv treated mice were diabetic, in contrast, 100% of control mice were diabetic (FIG. 4). In this example, 8 week old female NOD mice were injected with 50 µg of PV1-scFv or control antibody daily for 14 days.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method of downmodulating an autoimmune response in a subject having type I diabetes, comprising administering an effective amount of an antigen binding portion of an anti-CD28 antibody that blocks signaling via CD28 to the subject, such that an autoimmune response in the subject is downmodulated.

2. The method of claim 1, wherein the antigen binding portion is a scFv molecule or an Fab fragment.

3. The method of claim 1, wherein the antigen binding portion is humanized.

4. The method of claim 1, wherein the antigen binding portion is fully human.

5. A method of downmodulating an ongoing immune response in a subject having type I diabetes comprising administering an effective amount of an antigen binding portion of an anti-CD28 antibody that blocks signaling via CD28 to the subject, such that an ongoing autoimmune response in the subject is downmodulated.

6. The method of claim 5, wherein the antigen binding portion is a scFv molecule or an Fab fragment.

7. The method of claim 5, wherein the antigen-binding portion is humanized.

8. The method of claim 5, wherein the antigen-binding portion is fully human.

9. The method of claim 2, wherein the antigen binding portion is a scFv molecule.

10. The method of claim 9, wherein the scFv molecule is PV1.

11. The method of claim 6, wherein the antigen binding portion is a scFv molecule.

12. The method of claim 11, wherein the scFv molecule is PV1.

13. A method of downmodulating a CD28-mediated interaction in a subject having type I diabetes comprising administering an effective amount of an antigen binding portion of an anti-CD28 antibody that blocks signaling via CD28 to the subject, such that a CD28 interaction in the subject is downmodulated.

14. The method of claim 13, wherein the antigen binding portion is a scFv molecule or an Fab fragment.

15. The method of claim 13, wherein the antigen-binding portion is humanized.

16. The method of claim 13, wherein the antigen-binding portion is fully human.

17. The method of claim 13, wherein the antigen binding portion is a scFv molecule.

18. The method of claim 14, wherein the scFv molecule is PV1.

19. A method of downmodulating an autoimmune response in a subject having type I diabetes, comprising administering an effective amount of an antigen binding portion of an anti-CD28 antibody that blocks signaling via CD28 to the subject, such that an autoimmune response in the subject is downmodulated, wherein the antigen binding portion is a scFv molecule, and wherein the scFV molecule is PV1.

20. A method of downmodulating an ongoing immune response in a subject having type I diabetes comprising administering an effective amount of an antigen binding portion of an anti-CD28 antibody that blocks signaling via CD28 to the subject, such that an ongoing autoimmune response in the subject is downmodulated, wherein the antigen binding portion is a scFv molecule, and wherein the scFV molecule is PV1.

21. A method of downmodulating a CD28-mediated interaction in a subject having type I diabetes comprising administering an effective amount of an antigen binding portion of an anti-CD28 antibody that blocks signaling via CD28 to the subject, such that a CD28 interaction in the subject is downmodulated, wherein the antigen binding portion is a scFv molecule, and wherein the scFV molecule is PV1.

* * * * *

UNITED STATES PATENT AND TRADEMARK OFFICE
CERTIFICATE OF CORRECTION

PATENT NO. : 7,531,168 B2  Page 1 of 1
APPLICATION NO. : 10/076934
DATED : May 12, 2009
INVENTOR(S) : O'Hara et al.

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by 94 days Delete the phrase "by 94 days" and insert -- by 473 days --

Signed and Sealed this

Tenth Day of August, 2010

David J. Kappos
*Director of the United States Patent and Trademark Office*